United States Patent [19]
Simons

[11] Patent Number: 6,167,412
[45] Date of Patent: Dec. 26, 2000

[54] HANDHELD MEDICAL CALCULATOR AND MEDICAL REFERENCE DEVICE

[75] Inventor: Tad Decatur Simons, Palo Alto, Calif.

[73] Assignee: Agilent Technologies, Inc., Palo Alto, Calif.

[21] Appl. No.: 09/115,457

[22] Filed: Jul. 14, 1998

[51] Int. Cl.[7] .................................................. G06F 19/00
[52] U.S. Cl. .......................................... 708/105; 600/300
[58] Field of Search ...................... 708/105, 132, 708/200; 600/300, 481, 508, 529

[56] References Cited

U.S. PATENT DOCUMENTS

| | | | |
|---|---|---|---|
| 4,807,170 | 2/1989 | Kulli et al. | 364/413.01 |
| 5,265,010 | 11/1993 | Evans-Paganelli et al. | 364/413.02 |
| 5,404,292 | 4/1995 | Hendrickson | 364/413.02 |
| 5,630,664 | 5/1997 | Farrelly | 128/695 |
| 5,704,350 | 1/1998 | Williams, III | 708/132 |
| 5,729,479 | 3/1998 | Golan | 708/132 |
| 5,823,949 | 10/1998 | Goltra | 600/300 |
| 5,997,475 | 12/1999 | Bortz | 600/300 |

OTHER PUBLICATIONS

Apothecalc(TM) [Advertisement], NNCC, Inc., 100 Precision Court, Lancaster, KY 40444, p. 1.

PEPID [Advertisement], PEPID, Inc., Greenwood St., Evanston, IL 60201–4712, pp. 1–4.

Pocket PDR(TM) [Advertisement], Physician's Desk Reference, P.O. Box 824, Mahwah, NJ 07430, pp. 1–2.

Computer Books Medical Software [Advertisement], ComputerBooks, Newport Trade Centre, 20321 Irvine Avenue, Suite 2, P.O. Box 9167, Newport Beach, CA 92658–9986, pp. 1–2.

*Primary Examiner*—David H. Malzahn

[57] ABSTRACT

A handheld medical calculator and reference device having an input keypad and an output screen connected to a processor with memory to perform specific clinical functions. The clinical functions include: basic mathematical operations and common scientific functions for routine calculations; store/recall functions for numbers and for routinely used program settings; phone directory; user selection of display modes (fixed, scientific, choice of radix), degree/radian; time, date, and day of week features for timing and alarms (with display format choices); drug and infusion calculations; hemodynamic and cardiac functions; respiratory and pulmonary functions; acid-base functions; nutritional functions; nomograms, maps, and a reference table of normal values; and patient vital signs record keeping.

24 Claims, 26 Drawing Sheets

HANDHELD MEDICAL CALCULATOR AND MEDICAL REFERENCE DEVICE

TECHNICAL FIELD

The present invention relates generally to medical computers and more specifically to a handheld medical calculator and medical reference device for health care professionals.

BACKGROUND ART

Nurses, intensive care personnel, respiratory therapists, emergency room staff, paramedics, chemists, and other clinicians have certain things that they do all the time which must be done properly otherwise there may be serious consequences up to and including the death of a patient.

An example relates to drug and infusion calculations. A doctor issues prescriptions to clinicians based on the body weight of the patient since different size people take different amounts of drugs. A clinician must then get the drug from the pharmacy which provides it at a standard concentration and, looking at the order from a doctor and patient information on body weight, calculate precisely how much medication to give over a certain period of time. Sometimes, the dosages are based on body surface area and require further calculations and constants.

The calculations are often complex and require specific constants for dosages and infusions. Very experienced clinicians who have long experience will have memorized the constants, but newer clinicians or those who do not routinely work in the area will have to lookup the constants in a reference book in addition to performing the complex calculations. Thus, in addition to handheld calculators, these people usually must carry around little reference booklets which must fit the pockets in their lab coats.

In some cases where the prescriptions are routine, the clinicians will be provided with small charts to look up how much medication to give for a given body weight. However, even this is of limited value since many drugs are provided in solution at a specific concentration per volume of fluid, or a specific mass per tablet. A clinician must then compute the correct total dose for a patient. These calculations must often be performed with dimensioned units which must be converted into other comparable units in order to perform the calculations. For example, the prescription could be in terms of so many micrograms per square meter of body surface, while the drug concentration could be in milligrams per cubic centimeter. A mistake in the decimal point could kill a patient.

For some areas of medicine, a clinician will be told by a doctor to obtain certain medical data about a patient which are calculated from other parameters. These calculations are complex and often difficult to perform. An easy method to calculate these important parameters would benefit patient treatment. Cardiac, hemodynamic, respiratory and ventilatory calculations often fall into this category.

Another example is if a patient has been poisoned, and it is necessary to determine how long it takes for the toxins to wear off and how the patient is responding to treatment. There are complex relationships involved for which various nomograms have been developed for various toxins where observations are required over a timeframe.

Acid-base disorders also require complex calculations with several independent variables. These calculations in turn are often difficult to use and introduce mistakes into the treatment process.

For all health care professionals, handy drug references have long been desirable, but a comprehensive reference has had to be extremely bulky because of all the information and cross-references required. Computerized references have also been more convenient in laptop form, but the cross-referencing systems have made them difficult to use. Also, computers are not always available for clinicians. It is often not convenient to use laptop computers in a clinical setting, and they are relatively costly when compared to the cost of handheld calculators.

In the medical field, it is further necessary to have readily available the many different values of what constitutes the norm of the human physiology to determine how far off a patient is from normal. These values must be constantly referred to such that the small reference books regularly fall apart, become hard to read, and must be constantly replaced. Thus, a hand size reference has long been sought which provides easy accessibility and convenience.

A comprehensive solution for clinicians has long been sought which would ease their workload, simplify the complexity of the things they do, and reduce the life threatening errors, but such a solution has long eluded those skilled in the art.

DISCLOSURE OF THE INVENTION

The principal purpose of this device is to relieve the tedious and repetitive calculations and reference searches routinely performed by clinical staff. To achieve this purpose, the device is simple and inexpensive. There are many unused (shifted) keys that lend themselves to new functions and applications, but the device is kept simple. The medical users are often harried and tired, and a complicated design would diminish the utility of this device in a hospital or clinical setting. The device follows the style of specialized calculators, such as the scientific, business, and engineering calculators. The device is for clinicians and has the following functions in a format of selecting functions and receiving unambiguous, preconfigured prompts:

1. Basic mathematical operations and common scientific functions for routine calculations.
2. Store/Recall functions for numbers, and for routinely used program settings and a phone directory.
3. User selection of display modes (fixed, scientific, choice of radix), degree/radian, etc.
4. Time, date, day of week, and features for timing and alarms.
5. Drug and infusion calculations
6. Hemodynamic and cardiac functions.
7. Respiratory and pulmonary functions.
8. Acid-base functions.
9. Nutritional functions.
10. Common nomograms, and a reference table of normal values.
11. Patient vital signs record keeping.

The present invention has the advantage of being programmed with straightforward, preconfigured prompts of predetermined medical questions so the clinician does not have to do any programming or customizations.

The present invention has the additional advantage of having a softkey display for preconfigured prompts and related softkeys for simplified input of medical questions and information. Softkeys are so designated because they are keys programmed for different functions by internal software. While most of the input keys of the present invention have two functions based on their shifted or unshifted modes of operation, the softkeys have a plurality of functions based on the preconfigured prompts which appear as text on associated display areas.

The present invention has the additional advantage of providing a handheld device for performing complex drug calculations in a simple, straightforward manner.

The present invention has the additional advantage of providing a handheld device for performing complex drug and medical-related calculations in a simple, straightforward manner.

The present invention has the additional advantage of providing a handheld device for performing complex cardiac calculations in a simple, straightforward manner.

The present invention has the additional advantage of providing a handheld device for performing acid-base respiratory and nutritional calculations in a simple, straightforward manner.

The present invention has the additional advantage of providing a handheld device for providing complex medical reference information in a simple, straightforward manner.

The above and additional advantages of the present invention will become apparent to those skilled in the art from a reading of the following detailed description when taken in conjunction with the accompanying drawings.

BEST MODE FOR CARRYING OUT THE INVENTION

Figure 1:
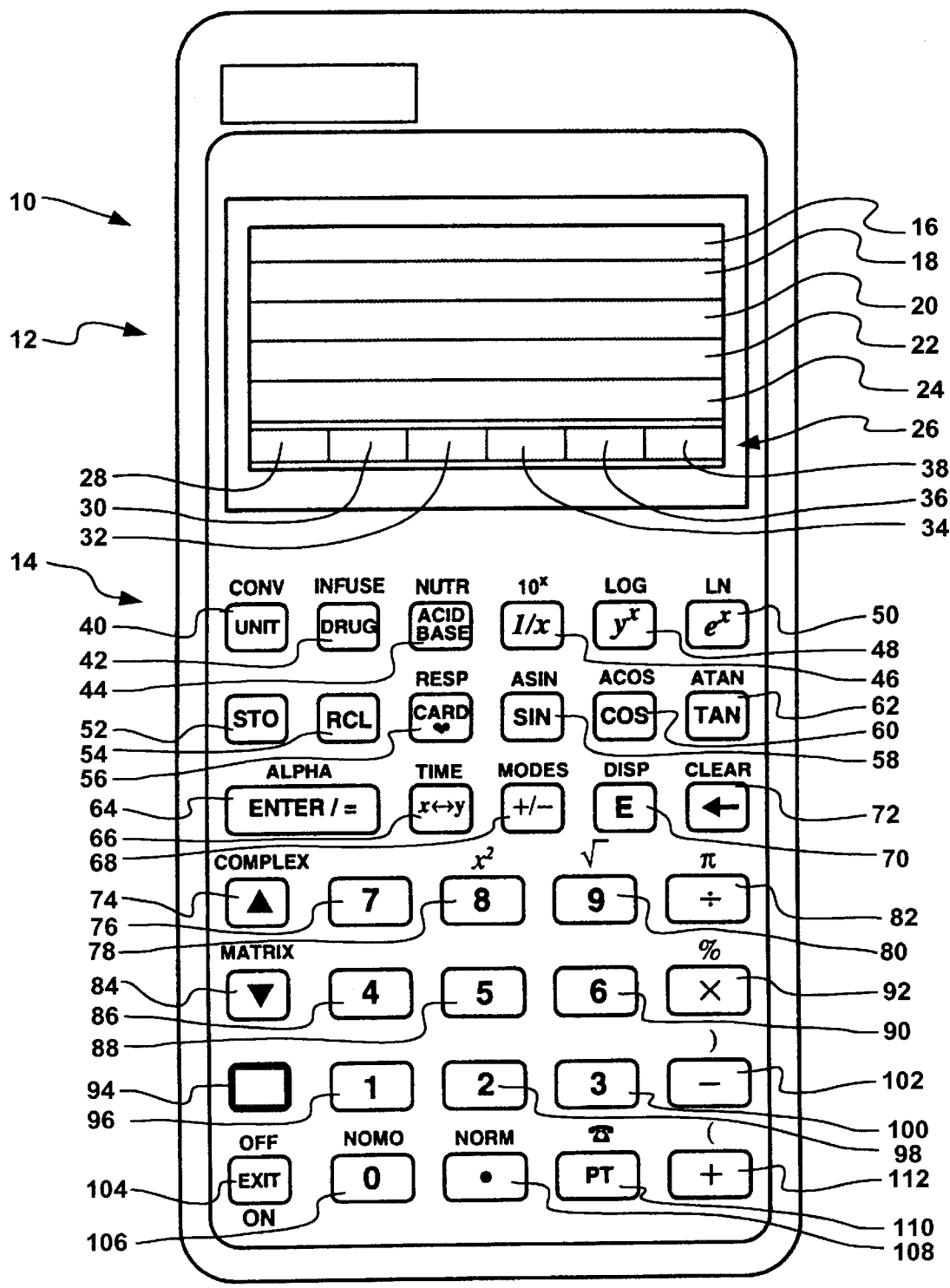
FIG. 1 is an embodiment of the present invention.

Referring now to FIG. 1, therein is shown the handheld medical calculator and medical reference device, referred to as the device 10. The device 10 has a high resolution, multi-character, output screen 12 and input keypad 14. It should be noted that the specific types and locations of the screen 12 and keypad 14 are optional with various types of lower resolution and ultrahigh resolution displays being useable as well as touch-sensitive displays and membrane keypads.

The screen 12 has a plurality of display lines 16, 18, 20, 22, and 24, and a softkey display line 26. The softkey display line 26 has six softkey title areas 28, 30, 32, 34, 36, and 38. These softkey title areas are where various preconfigured prompts appear, as will later be described. The prompts are preconfigured in that they are designed to make the device 10 operate intuitively and are not intended to be changed by the user.

The keypad 14 has a line of keys identified as softkeys 40, 42, 44, 46, 48, and 50 which are respectively below and which relate respectively to the softkey title areas 28, 30, 32, 34, 36, and 38. When there is a display on the softkey title areas 28, 30, 32, 34, 36, and 38, their respective softkeys 40, 42, 44, 46, 48, and 50 will be active in their sofikey modes.

The softkeys also have other functions where they do not function as softkeys and there are no displays in the softkey title areas although dedicated sofikeys would simplify the device 10. Dedicated softkeys would not have other functions. They would be dedicated for use only with the softkey title areas or for use in the unshifted mode. In the unshifted mode, their functions would be for the most popular series of calculations for which the device 10 is likely to be used.

Below, the softkeys are described in their non-softkey modes. The unshifted key functions and shifted key functions will first be described and then explained later.

The softkey 40 has a UNIT function and in the shifted position a CONV function. The softkey 42 has a DRUG function and, in the shifted position, a INFUSE function. The softkey 44 has an ACID BASE function and, in the shifted position, a NUTR function. The softkey 46 has a 1/x function and, in the shifted position, a $10^x$ function. The softkey 48 has a $y^x$ function and, in the shifted position a LOG function. The softkey 50 has a $e^x$ function and, in the shifted position, a LN function.

A first row of function keys 52, 54, 56, 58, 60, and 62 is below the softkeys. The function key 52 has a STO function and, in the shifted position, an opening for a function. The function key 54 has a RCL function and, in the shifted position, an opening for a function. The function key 56 has a CARD function and, in the shifted position, a RESP function. The function key 58 has a SIN function and, in the shifted position, an ASIN function. The function key 60 has a COS function and, in the shifted position, an ACOS function. The function key 62 has a TAN function and, in the shifted position, an ATAN function.

A row of second function keys 64, 66, 68, 70, and 72 is below the first row of function keys. The function key 64 has an ENTER/= function and, in the shifted position, an ALPHA function. The function key 66 has a x←→y function and, in the shifted position, a TIME function. The function key 68 has a +/− function and, in the shifted position, a MODES function. The function key 70 has an E function and, in the shifted position, a DISP function. The function key 72 has a ← function and, in the shifted position, a CLEAR function.

A first row of calculation keys 74, 76, 78, 80, and 82 is below the second row of function keys. The calculation key 74 has a ▲ which is an up scroll function and, in the shifted position a COMPLEX function. The calculation key 76 has a 7 which is a numerical entry function and, in the shifted position, an opening for a function. The calculation key 78 has a 8 which is a numerical entry function and, in the shifted position, a $x^2$ function. The calculation key 80 has a 9 which is a numerical entry function and, in the shifted position, an √which is a square root function. The calculation key 82 has a ÷ which is a divide function and, in the shifted position, a π function.

A second row of calculation keys 84, 86, 88, 90, and 92 is below the first row of calculation keys. The calculation key 84 has a ▼ which is a down scroll function and, in the shifted position a MATRIX function. The calculation key 86 has a 4 which is a numerical entry function and, in the shifted position, an opening for a function. The calculation key 88 has a 5 which is a numerical entry function and, in the shifted position, an opening for a function. The calculation key 90 has a 6 which is a numerical entry function and, in the shifted position, an an opening for a function. The calculation key 92 has an X which is a multiply function and, in the shifted position, a % function.

A third row of calculation keys 94, 96, 98, 100, and 102 is below the second row of calculation keys. The calculation key 94 has a ■ which is the shift key for selecting in the unshifted position the functions labeled on the keys or for selecting in the shifted position the functions labled over the keys. The calculation key 96 has a 1 which is a numerical entry function and, in the shifted position, an opening for a function. The calculation key 98 has a 2 which is a numerical entry function and, in the shifted position, an opening for a function. The calculation key 100 has a 2 which is a numerical entry function and, in the shifted position, an opening for a function. The calculation key 102 has an − which is a subtract function and, in the shifted position, a) close parenthesis function.

A bottom row of keys 104, 106, 108, 110, and 112 is below the third row of calculation keys. The key 104 has a EXIT function and it is also the ON and OFF function key. The key 106 has a 0 which is a numerical entry function and, in the shifted position, a NOMO function for accessing various nomograms. The key 108 has a . which is the decimal point entry function and, in the shifted position, a NORM function to provide information on normal values. The key 110 has a PT patient function and, in the shifted position, a ☎ telephone function. The key 112 has an + which is an add function and, in the shifted position, a ( open parenthesis function. Internally (and thus not shown), is a simple processing unit and electronic memory. The memory is loaded with dedicated medical software for the processing unit and with medical reference material.

Figure 2:
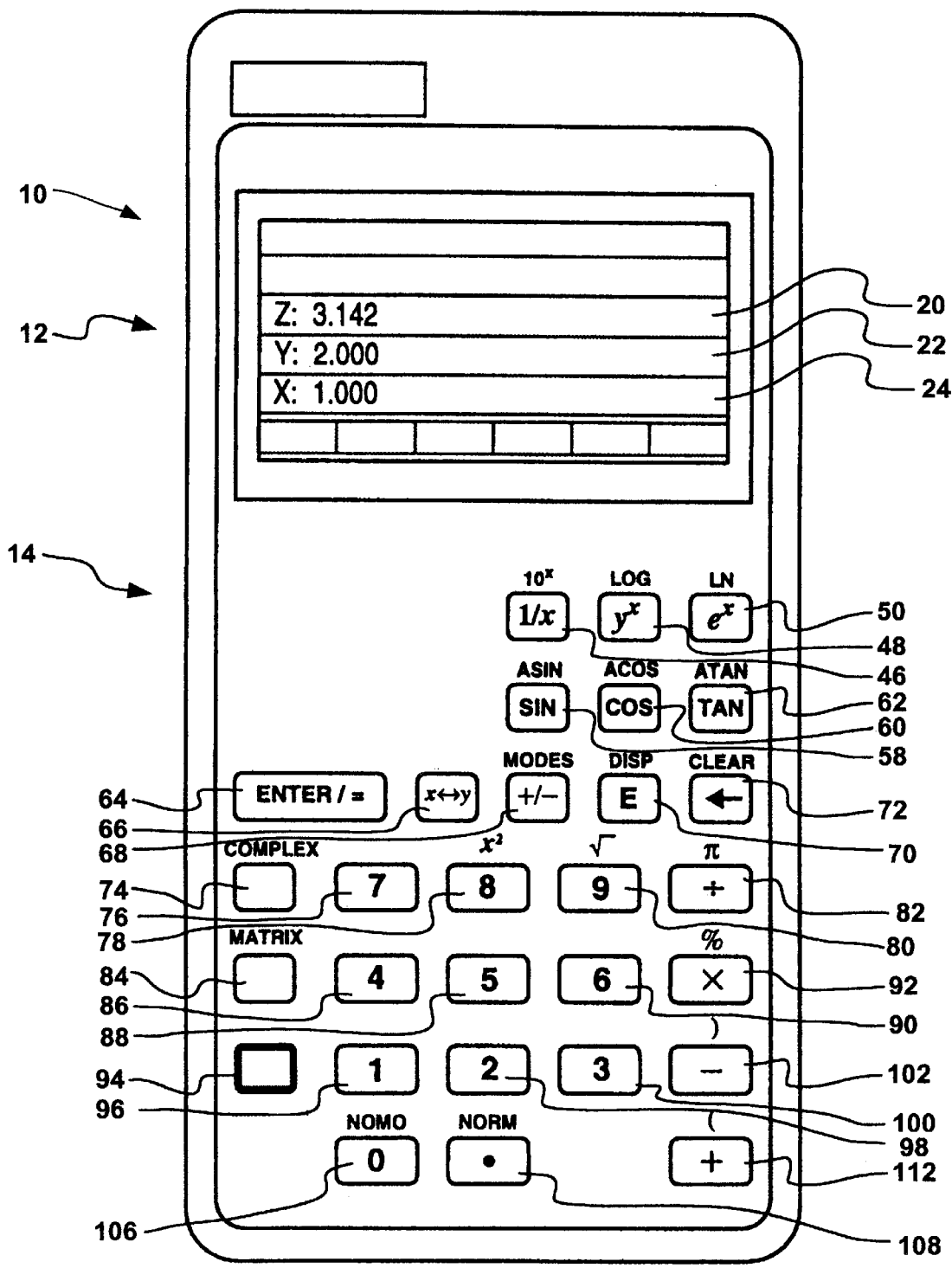
FIG. 2 is the portion of the embodiment used for the basic mathematical calculator functions.

Referring now to FIG. 2, therein is shown the device 10 with the screen 12 and the keypad 14 used for the basic mathematical calculator functions numbered with the same numbers as in FIG. 1.

Figure 3:
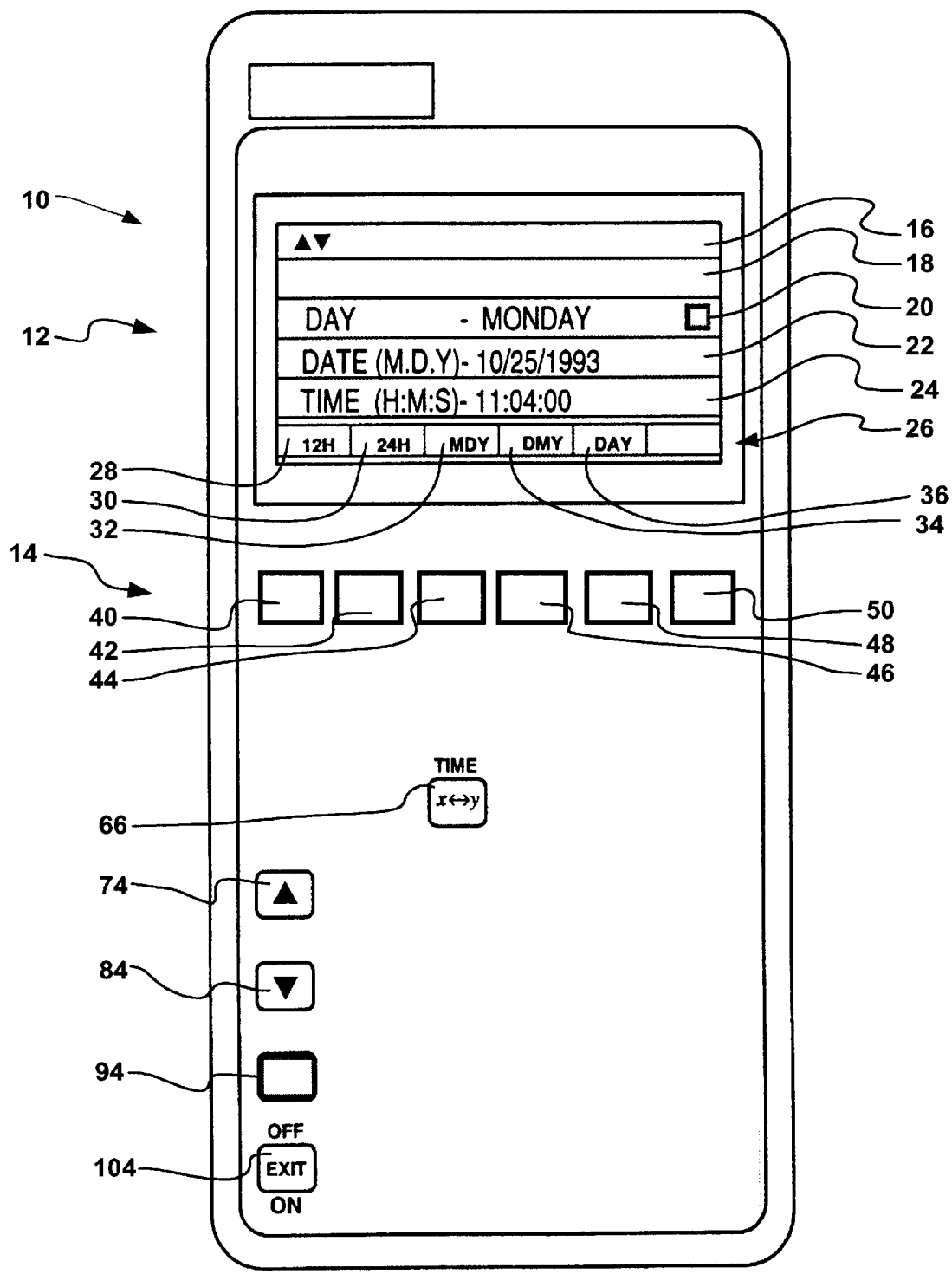
FIG. 3 is the portion of the device used for the time and medical time functions.

Referring now to FIG. 3, therein is shown the device 10 with the screen 12 and the keypad 14 used for the time and medical time functions numbered with the same numbers as in FIG. 1.

Figure 4:
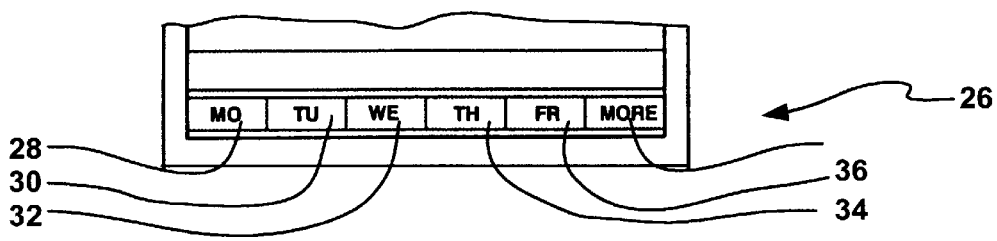
FIG. 4, is the bottom of the screen of the device resulting from one selection of the keys used for the time and medical time functions.

Referring now to FIG. 4, therein is shown the bottom of screen 12 resulting from one selection of the keypad 14 used for the time and medical time functions numbered with the same numbers as in FIG. 1.

Figure 5:
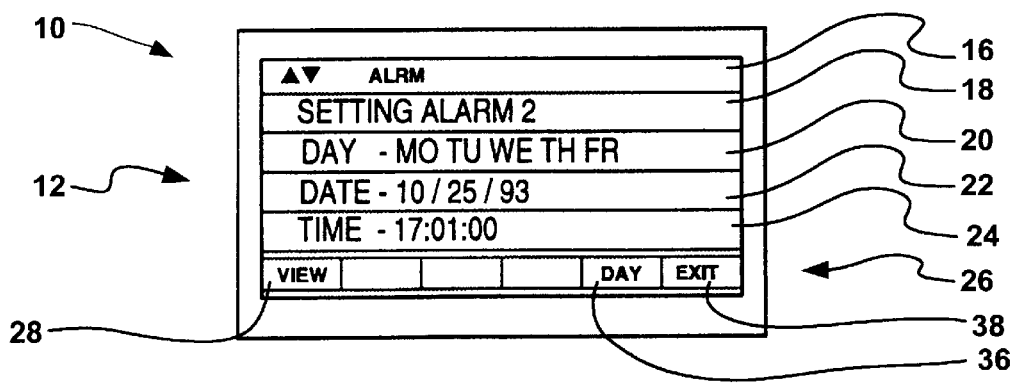
FIG. 5, is the screen resulting from another selection of the keys used for the time and medical time functions.

Referring now to FIG. 5, therein is shown the screen 12 resulting from another selection of the keypad 14 used for the time and medical time functions numbered with the same numbers as in FIG. 1.

Figure 6:
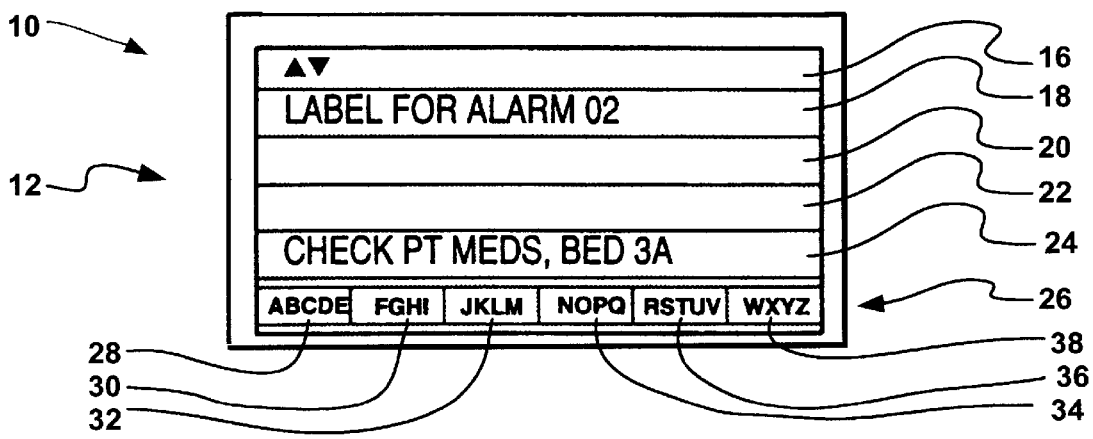
FIG. 6 is the screen resulting from another selection of the keys used for the time and medical time functions.

Referring now to FIG. 6, therein is shown the screen 12 resulting from another selection of the keypad 14 used for the time and medical time functions numbered with the same numbers as in FIG. 1.

Figure 7:
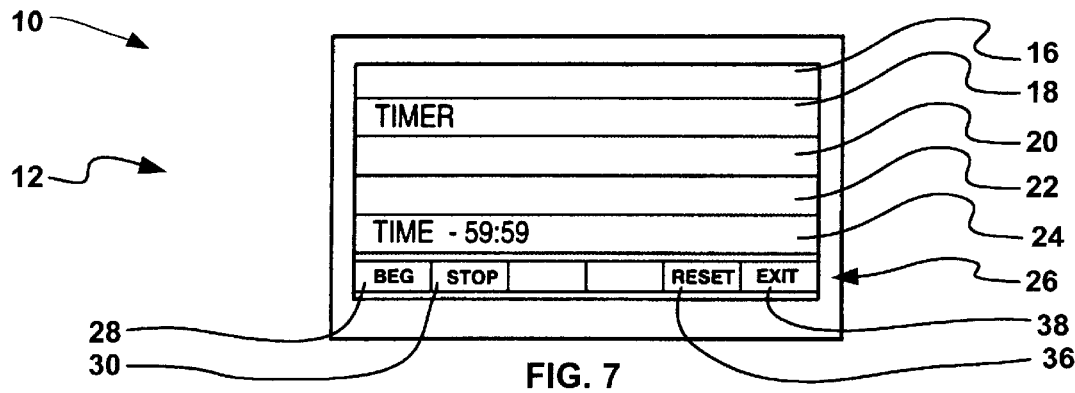
FIG. 7 is the screen resulting from another selection of the keys used for the time and medical time functions.

Referring now to FIG. 7, therein is shown the screen 12 resulting from another selection of the keypad 14 used for the time and medical time functions numbered with the same numbers as in FIG. 1.

Figure 8:
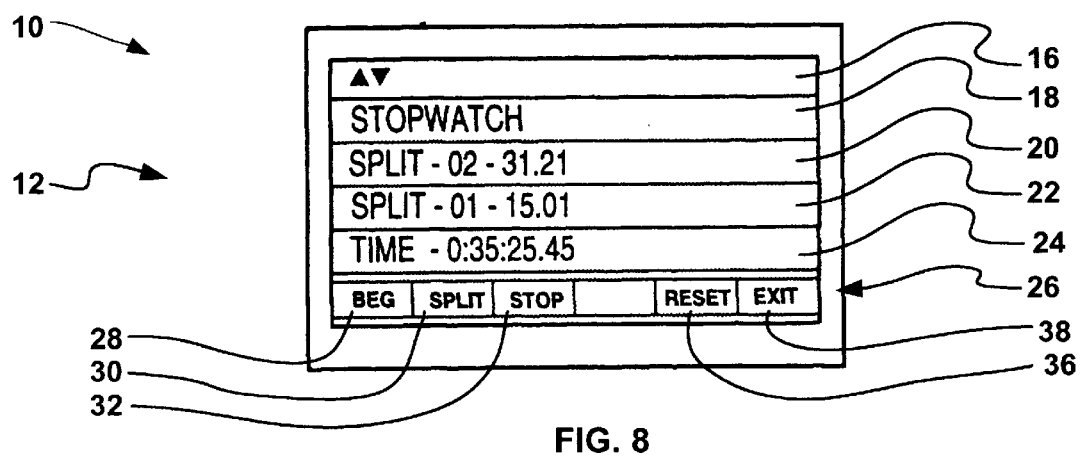
FIG. 8 is the screen resulting from another selection of the keys used for the time and medical time.

Referring now to FIG. 8, therein is shown the screen 12 resulting from one selection of the keypad 14 used for the time and medical time functions numbered with the same numbers as in FIG. 1.

Figure 9:
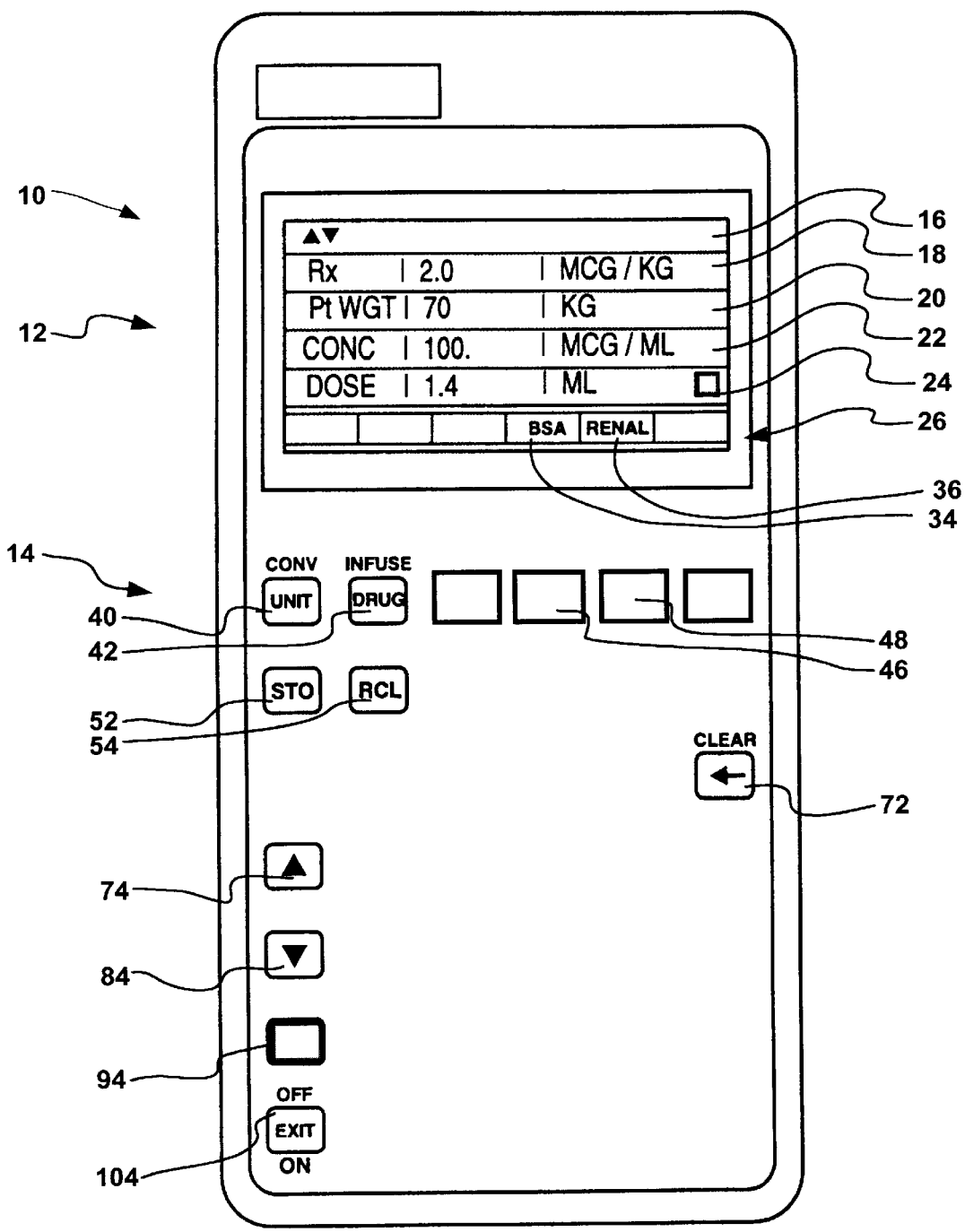
FIG. 9 is the portion of the device used for the drug and infusion calculation functions.

Referring now to FIG. 9, therein is shown the device 10 with the screen 12 and the keypad 14 used for the drug and infusion calculation functions numbered with the same numbers as in FIG. 1.

Figure 10:
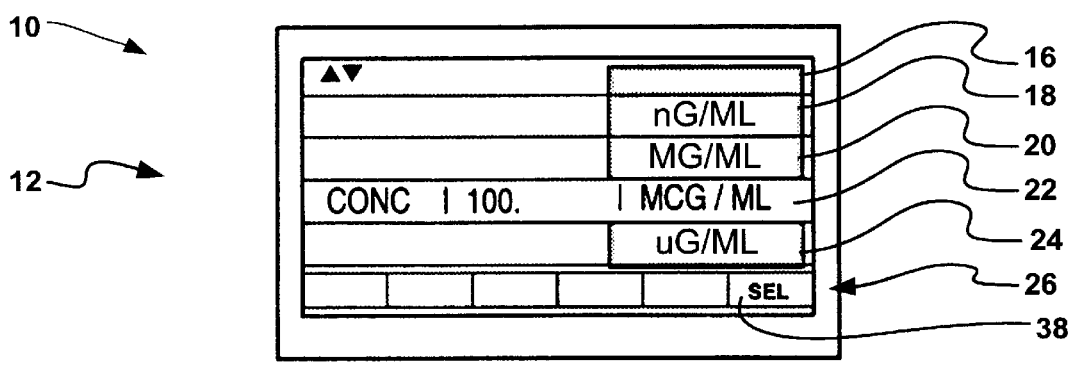
FIG. 10 is the screen resulting from another selection of the keys used for the drug and infusion calculation functions.

Referring now to FIG. 10, therein is shown the screen 12 resulting from one selection of the keypad 14 used for the drug and infusion calculation functions numbered with the same numbers as in FIG. 1.

Referring now to FIG. 1, therein is shown the screen 12 resulting from one selection of the keypad 14 used for the drug and infusion calculation functions numbered with the same numbers as in FIG. 1.

Figure 12:
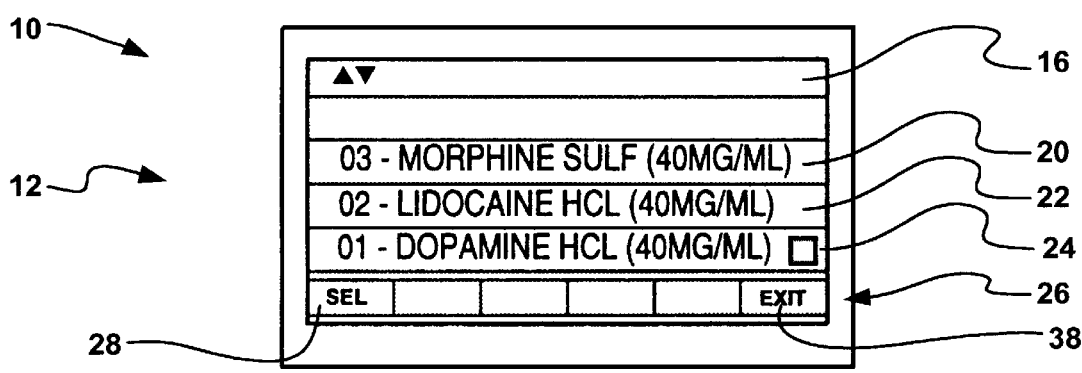
FIG. 12 is the screen resulting from another selection of the keys used for the drug and infusion calculation functions.

Referring now to FIG. 12, therein is shown the screen 12 resulting from another selection of the keypad 14 used for the drug and infusion calculation functions numbered with the same numbers as in FIG. 1.

Figure 13:
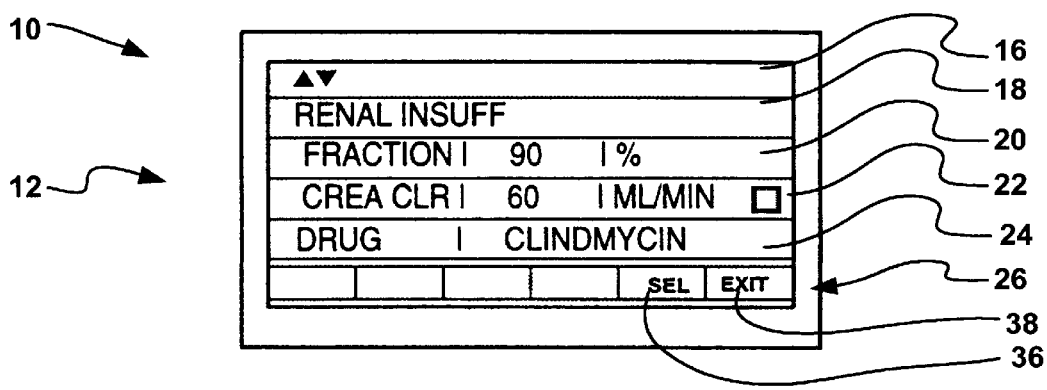
FIG. 13 is the screen resulting from another selection of the keys used for the drug and infusion calculation functions.

Referring now to FIG. 13, therein is shown the screen 12 resulting from another selection of the keypad 14 used for the drug and infusion calculation functions numbered with the same numbers as in FIG. 1.

Figure 14:
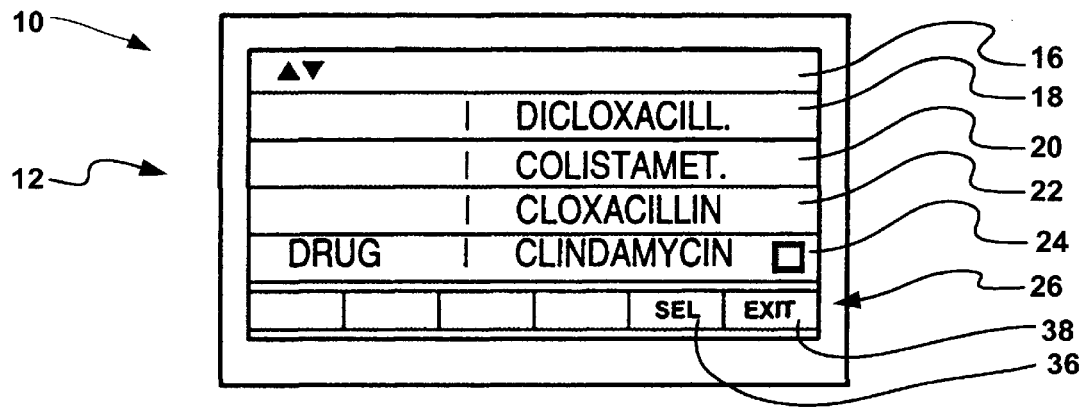
FIG. 14 is the screen resulting from another selection of the keys used for the drug and infusion calculation functions.

Referring now to FIG. 14, therein is shown the screen 12 resulting from another selection of the keypad 14 used for the drug and infusion calculation functions numbered with the same numbers as in FIG. 1.

Figure 15:
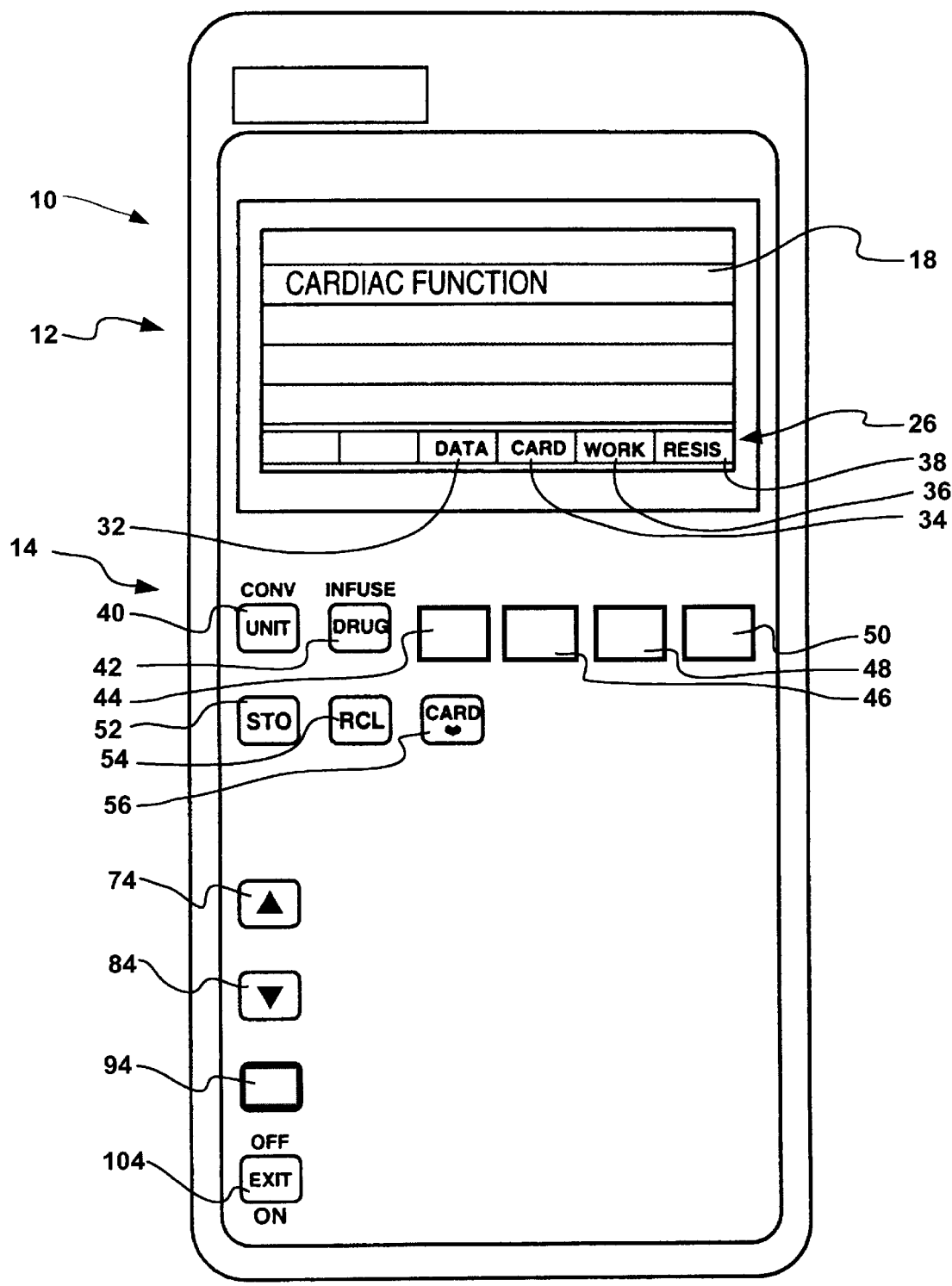
FIG. 15 is the portion of the device used for the cardiac function calculations.

Referring now to FIG. 15, therein is shown the device 10 with the screen 12 and the keypad 14 used for the cardiac function calculations numbered with the same numbers as in FIG. 1.

Figure 16:
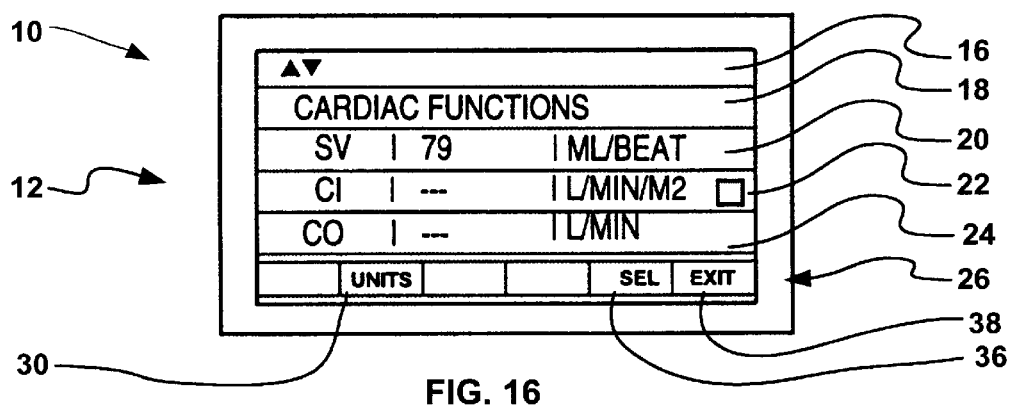
FIG. 16 is the screen resulting from another selection of the keys used for the cardiac function calculations.

Referring now to FIG. 16, therein is shown the screen 12 resulting from one selection of the keypad 14 used for the cardiac function calculations numbered with the same numbers as in FIG. 1.

Figure 17:
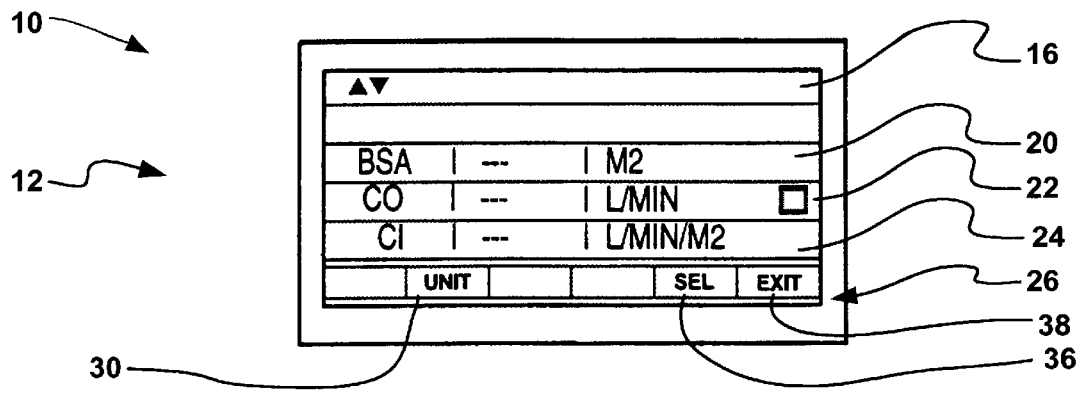
FIG. 17 is the screen resulting from another selection of the keys used for the cardiac function calculations.

Referring now to FIG. 17, therein is shown the screen 12 resulting from another selection of the keypad 14 used for the cardiac function calculations numbered with the same numbers as in FIG. 1.

Figure 18:
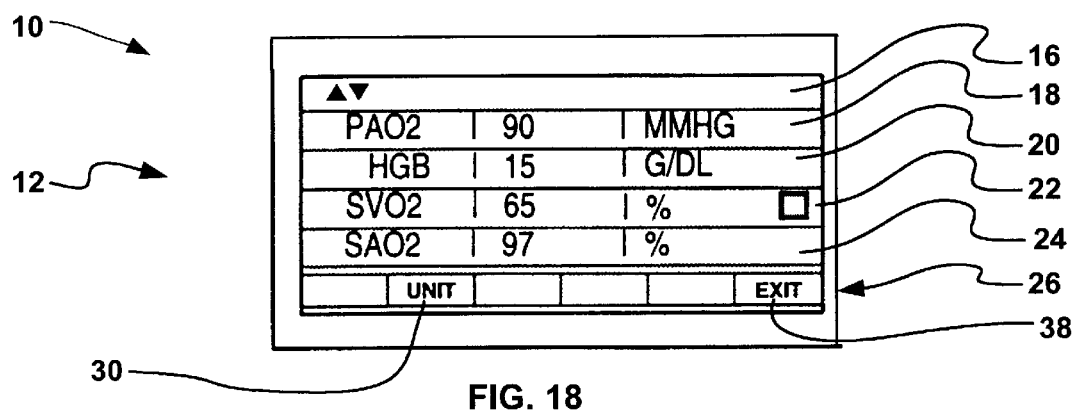
FIG. 18 is the screen resulting from another selection of the keys used for the cardiac function calculations.

Referring now to FIG. 18, therein is shown the screen 12 resulting from another selection of the keypad 14 used for the cardiac function calculations numbered with the same numbers as in FIG. 1.

Figure 19:
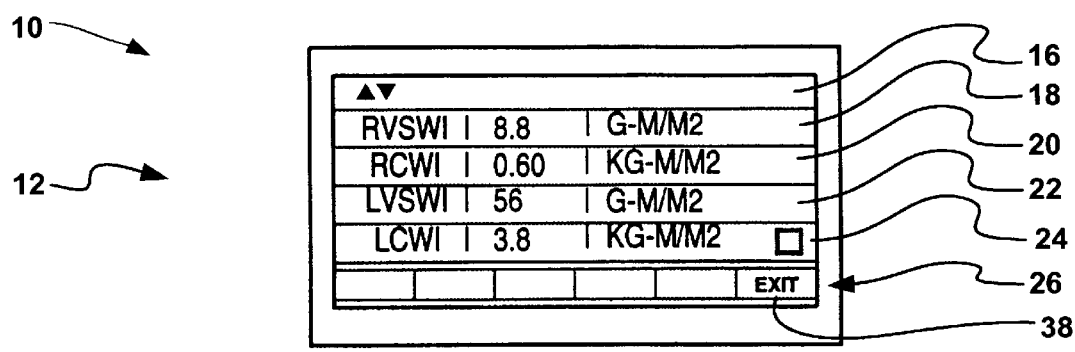
FIG. 19 is the screen resulting from another selection of the keys used for the cardiac function calculations.

Referring now to FIG. 19, therein is shown the screen 12 resulting from another selection of the keypad 14 used for the cardiac function calculations numbered with the same numbers as in FIG. 1.

Figure 20:
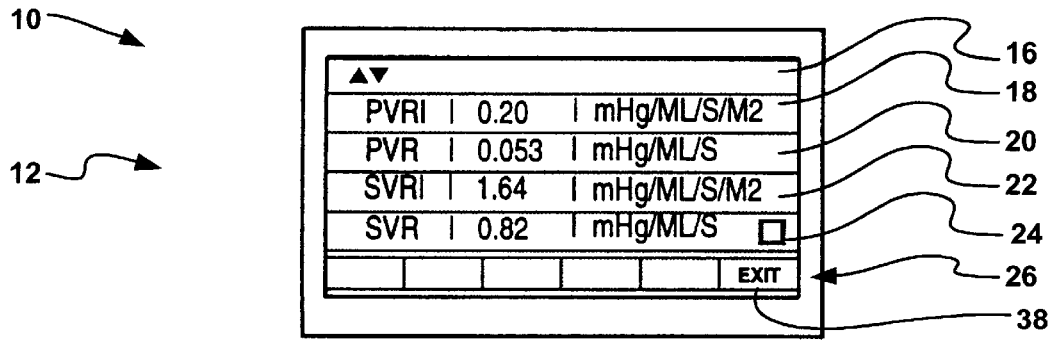
FIG. 20 is the screen resulting from another selection of the keys used for the cardiac function calculations.

Referring now to FIG. 20, therein is shown the screen 12 resulting from another selection of the keypad 14 used for the cardiac function calculations numbered with the same numbers as in FIG. 1.

Figure 21:
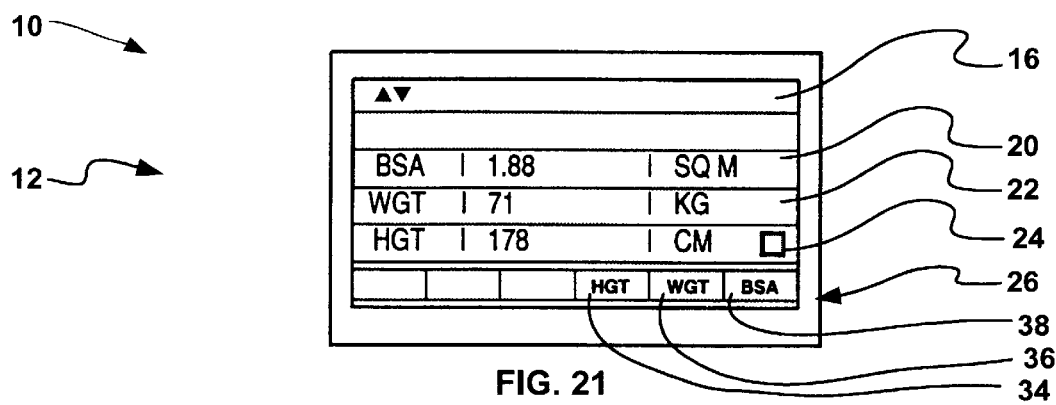
FIG. 21 is the screen resulting from another selection of the keys used for the cardiac function calculations.

Referring now to FIG. 21, therein is shown the screen 12 resulting from another selection of the keypad 14 used for the cardiac function calculations numbered with the same numbers as in FIG. 1.

Figure 22:
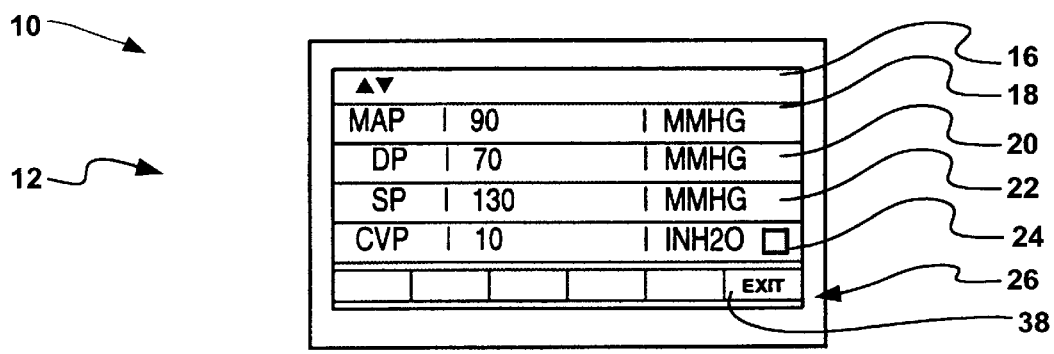
FIG. 22 is the screen resulting from another selection of the keys used for the cardiac function calculations.

Referring now to FIG. 22, therein is shown the screen 12 resulting from another selection of the keypad 14 used for the cardiac function calculations numbered with the same numbers as in FIG. 1.

Figure 23:
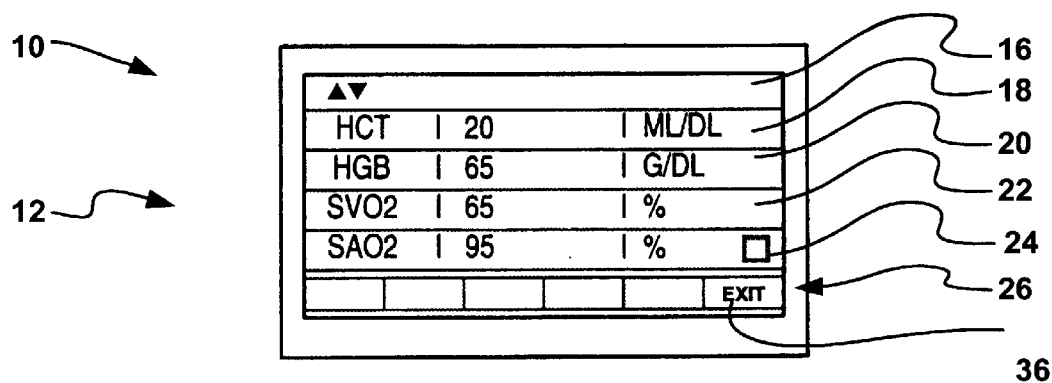
FIG. 23 is the screen resulting from another selection of the keys used for the cardiac function calculations.

Referring now to FIG. 23, therein is shown the screen 12 resulting from another selection of the keypad 14 used for the cardiac function calculations numbered with the same numbers as in FIG. 1.

Figure 24:
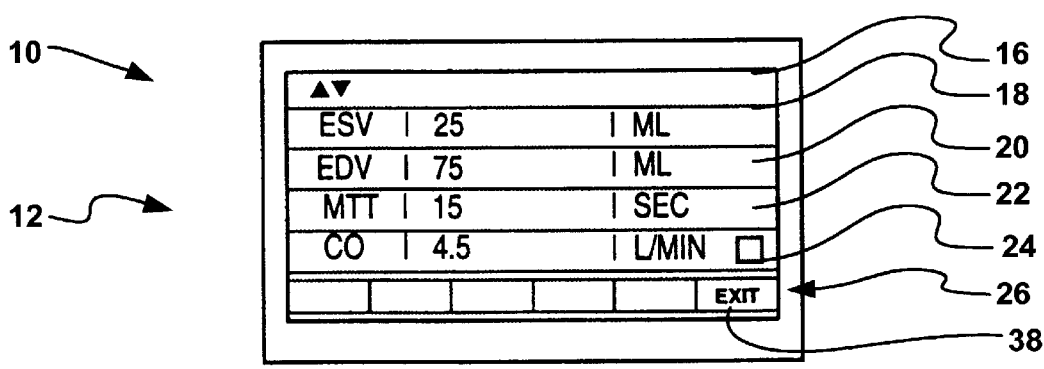
FIG. 24 is the screen resulting from another selection of the keys used for the cardiac function calculations.

Referring now to FIG. 24, therein is shown the screen 12 resulting from another selection of the keypad 14 used for the cardiac function calculations numbered with the same numbers as in FIG. 1.

Figure 25:
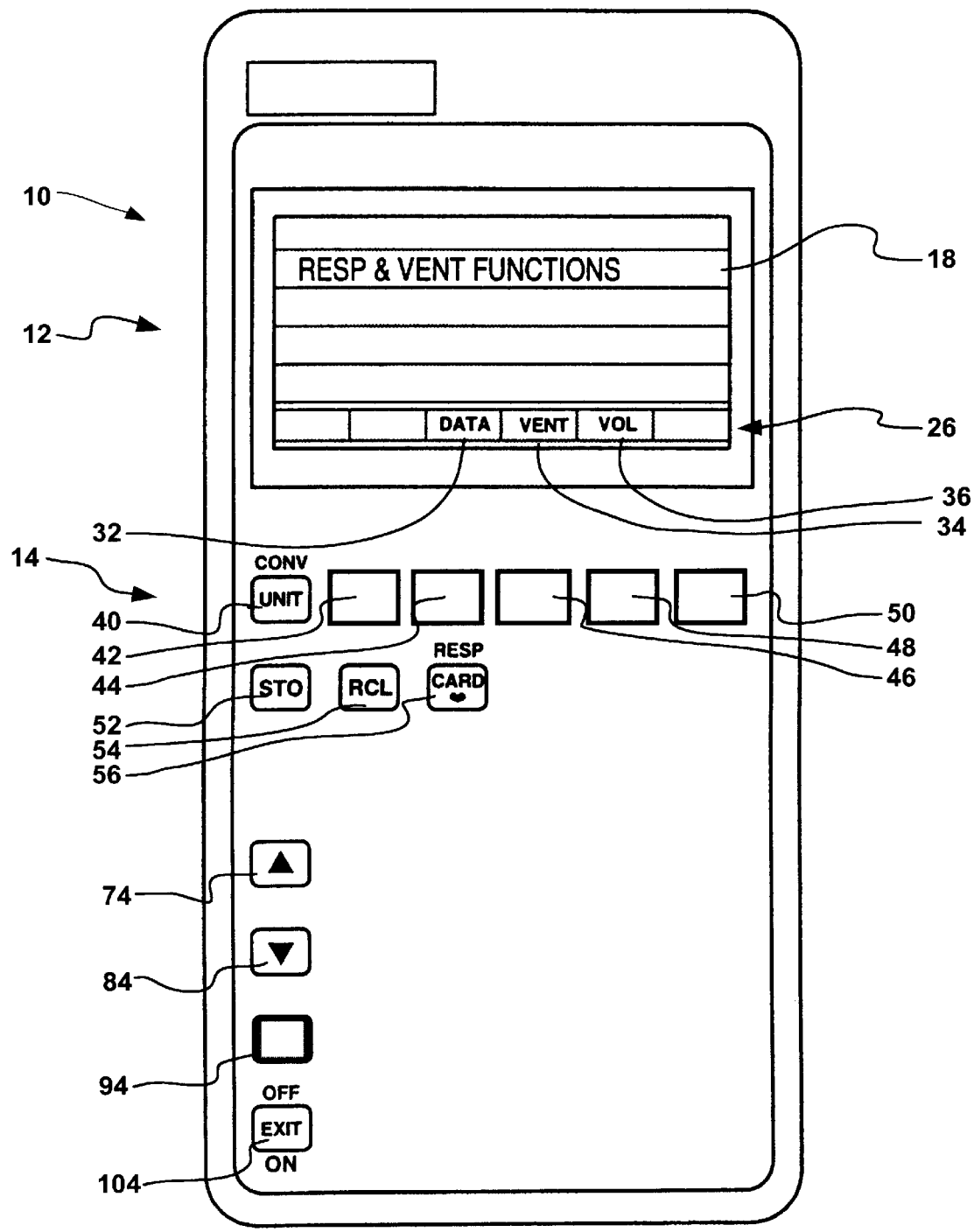
FIG. 25 is the portion of the device used for the respiratory calculations.

Referring now to FIG. 25, therein is shown the device 10 with the screen 12 and the keypad 14 used for the respiratory calculations numbered with the same numbers as in FIG. 1.

Figure 26:
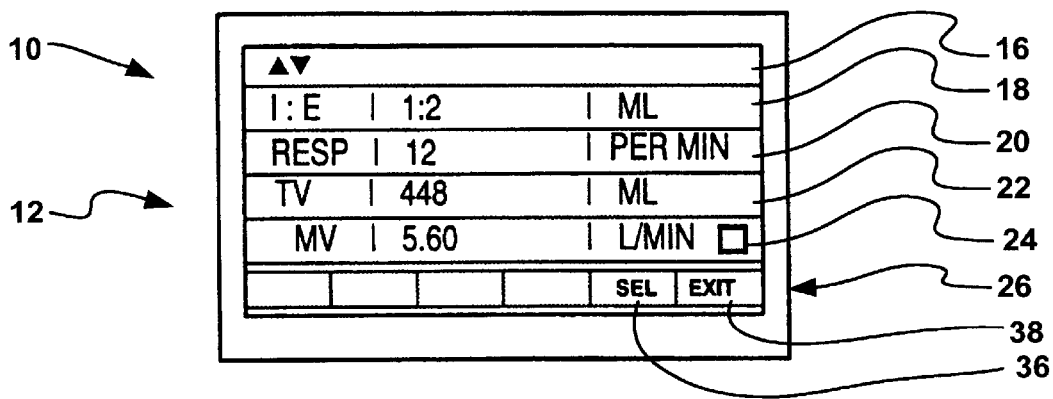
FIG. 26 is the screen resulting from another selection of the keys used for the respiratory calculations.

Referring now to FIG. 26, therein is shown the screen 12 resulting from another selection of the keypad 14 used for the respiratory calculations numbered with the same numbers as in FIG. 1.

Figure 27:
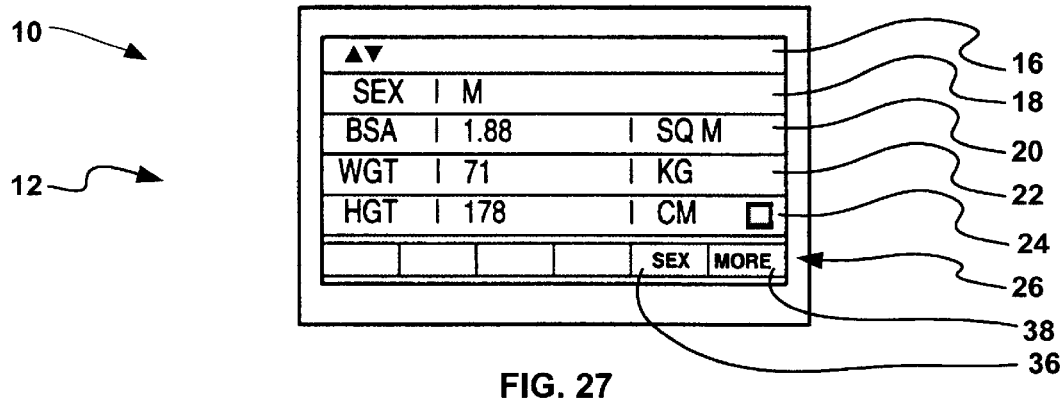
FIG. 27 is the screen resulting from another selection of the keys used for the respiratory calculations.

Referring now to FIG. 27, therein is shown the screen 12 resulting from another selection of the keypad 14 used for the respiratory calculations numbered with the same numbers as in FIG. 1.

Figure 28:
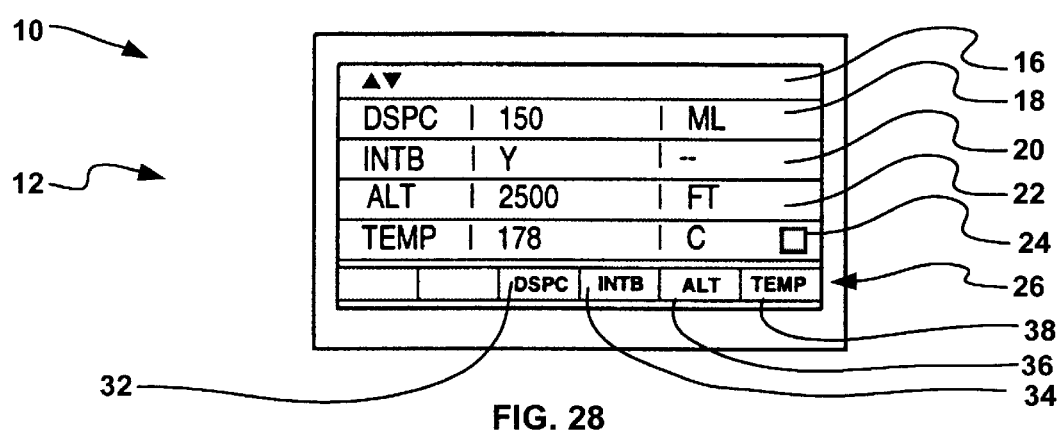
FIG. 28 is the screen resulting from another selection of the keys used for the respiratory calculations.

Referring now to FIG. 28, therein is shown the screen 12 resulting from another selection of the keypad 14 used for the respiratory calculations numbered with the same numbers as in FIG. 1.

Figure 29:
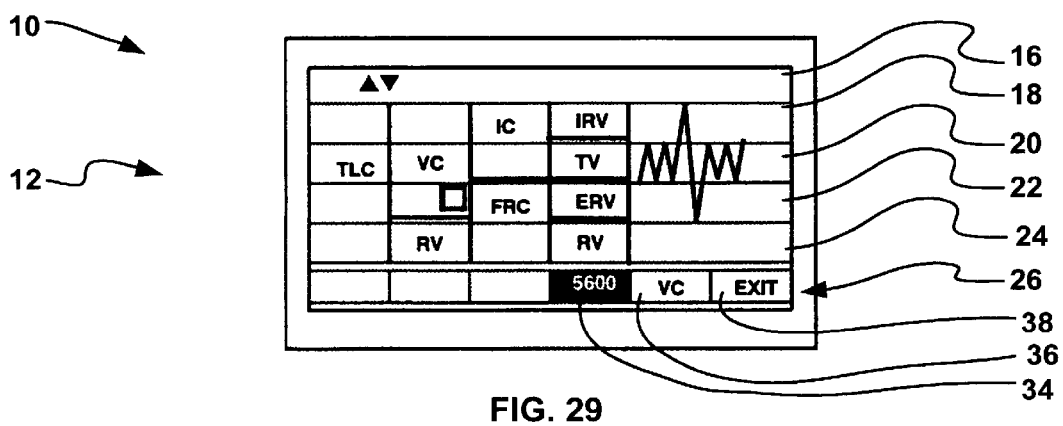
FIG. 29 is the screen resulting from another selection of the keys used for the respiratory calculations.

Referring now to FIG. 29, therein is shown the screen 12 resulting from another selection of the keypad 14 used for the respiratory calculations numbered with the same numbers as in FIG. 1.

Figure 30:
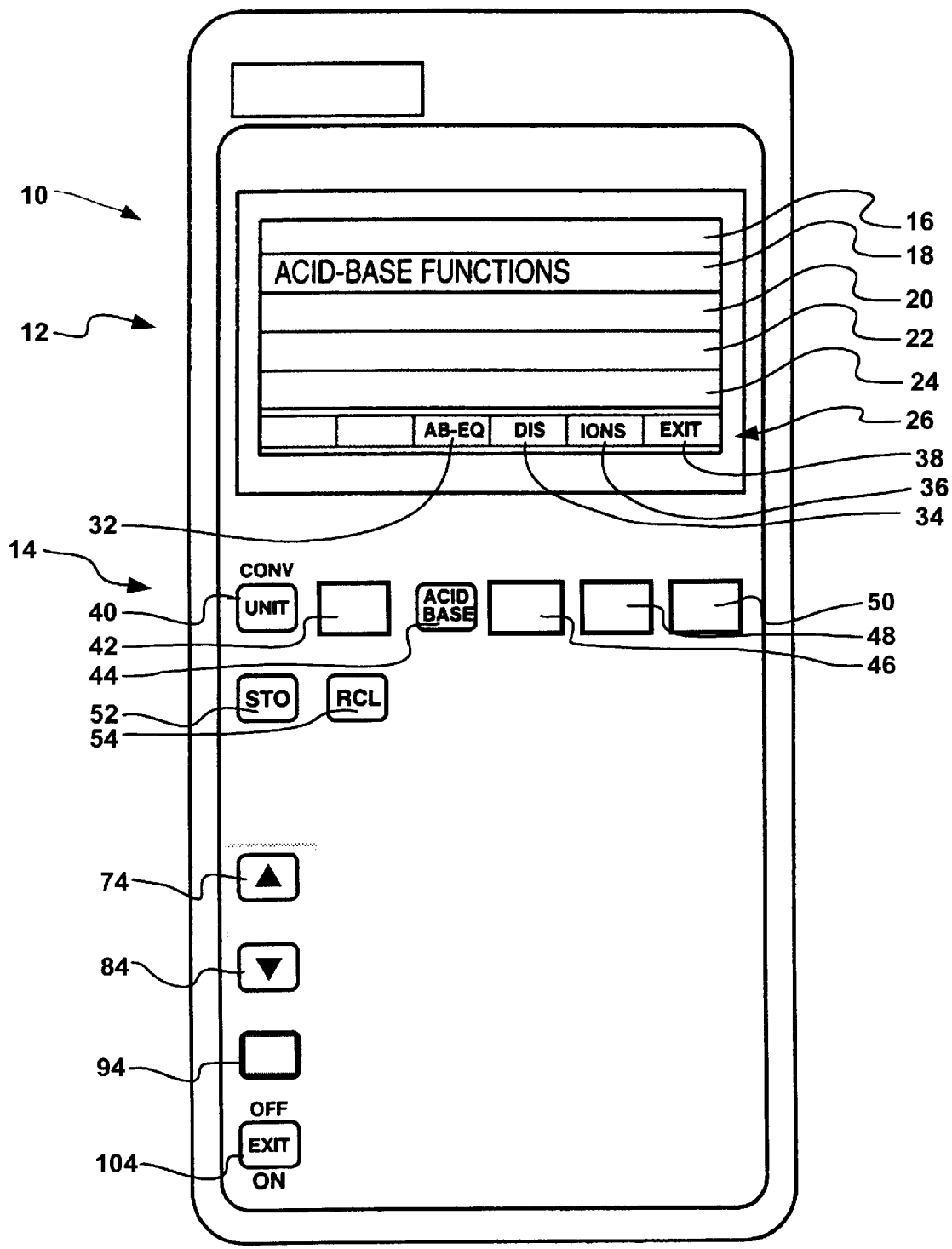
FIG. 30 is the portion of the device used for the acid-base calculations.

Referring now to FIG. 30, therein is shown the device 10 with the screen 12 and the keypad 14 used for the acid-base calculations numbered with the same numbers as in FIG. 1.

Figure 31:
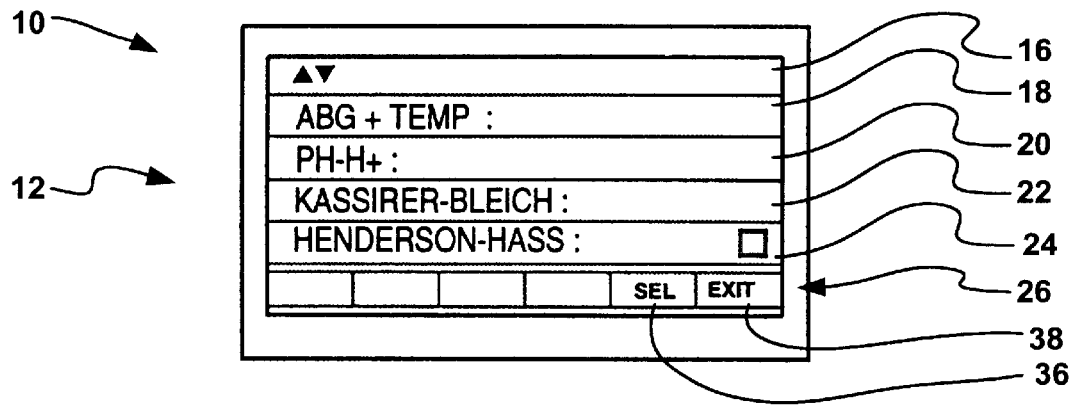
FIG. 31 is the screen resulting from another selection of the keys used for the acid-base calculations.

Referring now to FIG. 31, therein is shown the screen 12 resulting from another selection of the keypad 14 used for the acid-base calculations numbered with the same numbers as in FIG. 1.

Figure 32:
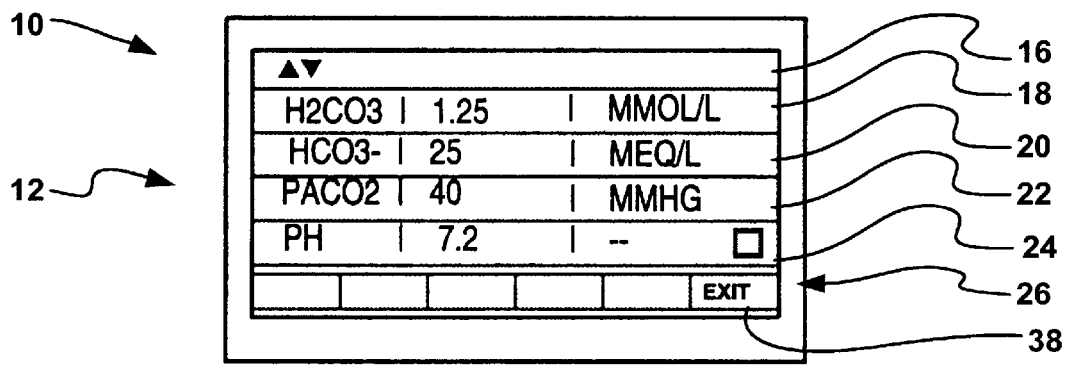
FIG. 32 is the screen resulting from another selection of the keys used for the acid-base calculations.

Referring now to FIG. 32, therein is shown the screen 12 resulting from another selection of the keypad 14 used for the acid-base calculations numbered with the same numbers as in FIG. 1.

Figure 33:
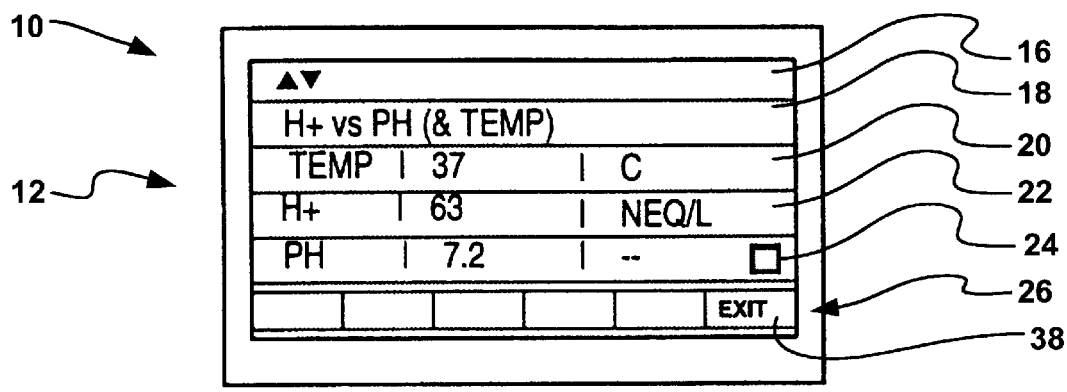
FIG. 33 is the screen resulting from another selection of the keys used for the acid-base calculations.

Referring now to FIG. 33, therein is shown the screen 12 resulting from another selection of the keypad 14 used for the acid-base calculations numbered with the same numbers as in FIG. 1.

Figure 34:
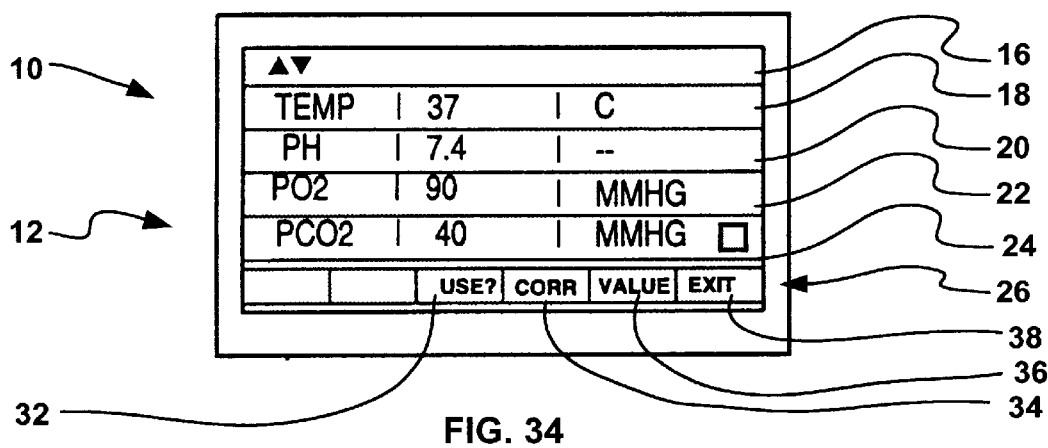
FIG. 34 is the screen resulting from another selection of the keys used for the acid-base calculations.

Referring now to FIG. 34, therein is shown the screen 12 resulting from another selection of the keypad 14 used for the acid-base calculations numbered with the same numbers as in FIG. 1.

Figure 35:
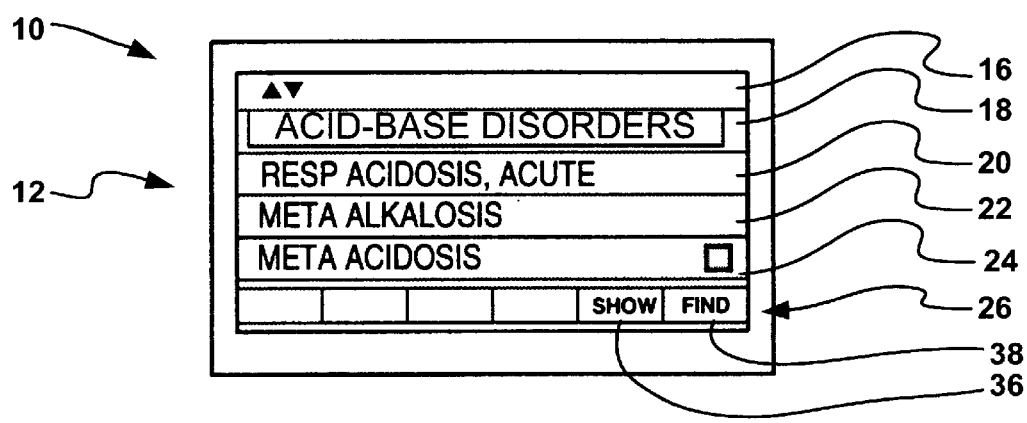
FIG. 35 is the screen resulting from another selection of the keys used for the acid-base calculations.

Referring now to FIG. 35, therein is shown the screen 12 resulting from another selection of the keypad 14 used for the acid-base calculations numbered with the same numbers as in FIG. 1.

Figure 36:
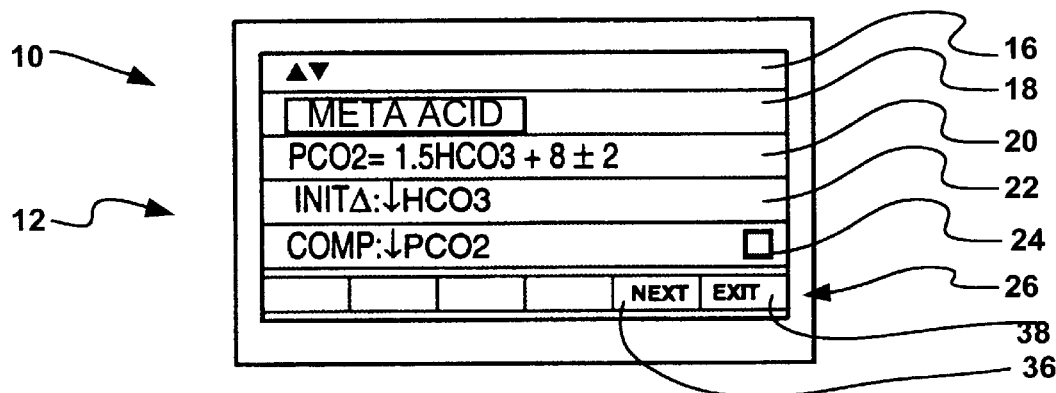
FIG. 36 is the screen resulting from another selection of the keys 1 used for the acid-base calculations.

Referring now to FIG. 36, therein is shown the screen 12 resulting from another selection of the keypad 14 used for the acid-base calculations numbered with the same numbers as in FIG. 1.

Figure 37:
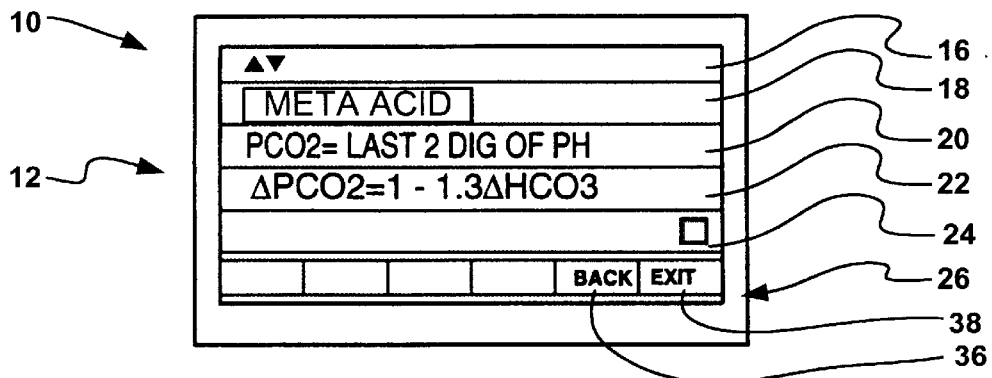
FIG. 37 is the screen resulting from another selection of the keys used for the acid-base calculations.

Referring now to FIG. 37, therein is shown the screen 12 resulting from another selection of the keypad 14 used for the acid-base calculations numbered with the same numbers as in FIG. 1.

Figure 38:
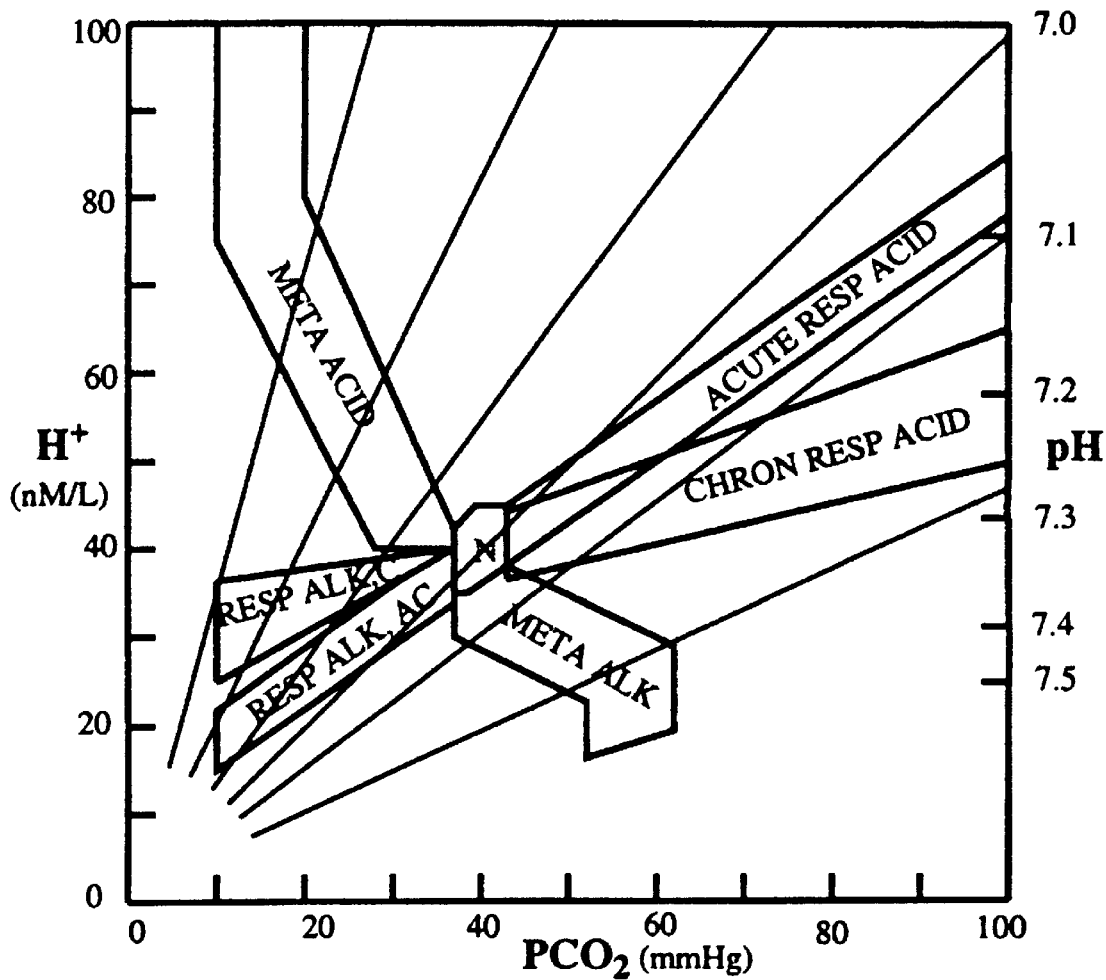
FIG. 38 is a screen which shows a map which could result from another selection of the keys used for the acid-base calculations.

Referring now to FIG. 38, therein is shown the screen 12 resulting from another selection of the keypad 14 used for the acid-base calculations numbered with the same numbers as in FIG. 1. This screen 12 shows a map of acid-base conditions from which the device 10 outputs specific information on the state of a patient and gives corrective instructions which is possible with a high resolution screen.

Figure 39:
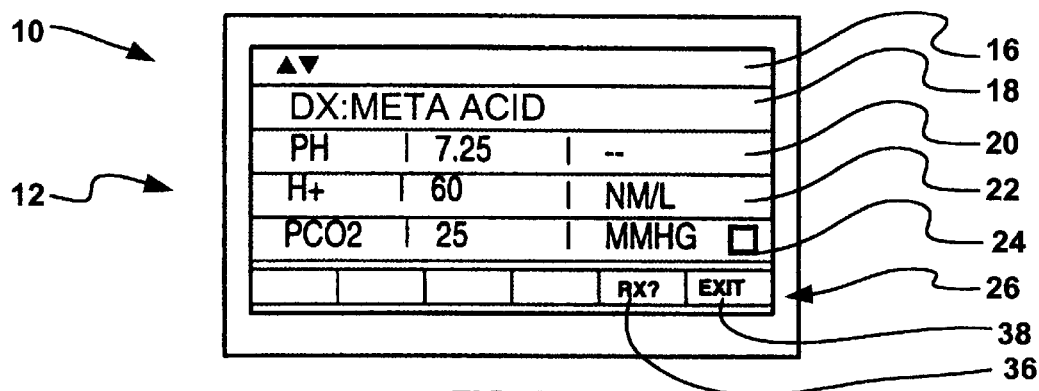
FIG. 39 is the screen resulting from another selection of the keys used for the acid-base calculations.

Referring now to FIG. 39, therein is shown the screen 12 resulting from another selection of the keypad 14 used for the acid-base calculations numbered with the same numbers as in FIG. 1.

Figure 40:
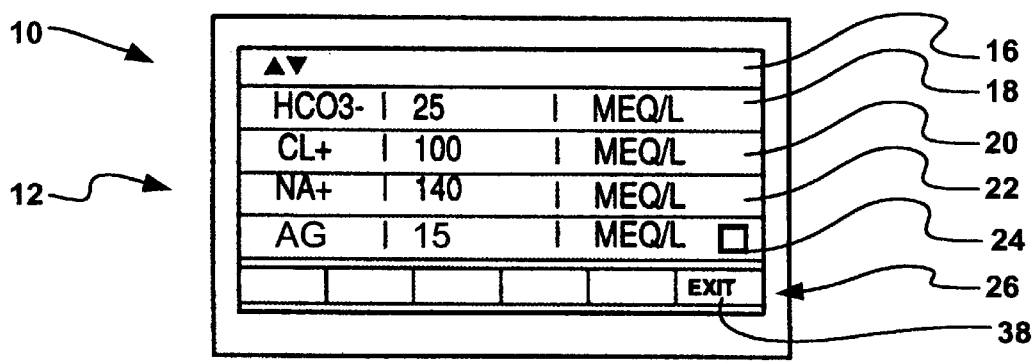
FIG. 40 is the screen resulting from another selection of the keys used for the acid-base calculations.

Referring now to FIG. 40, therein is shown the screen 12 resulting from another selection of the keypad 14 used for the acid-base calculations numbered with the same numbers as in FIG. 1.

Figure 41:
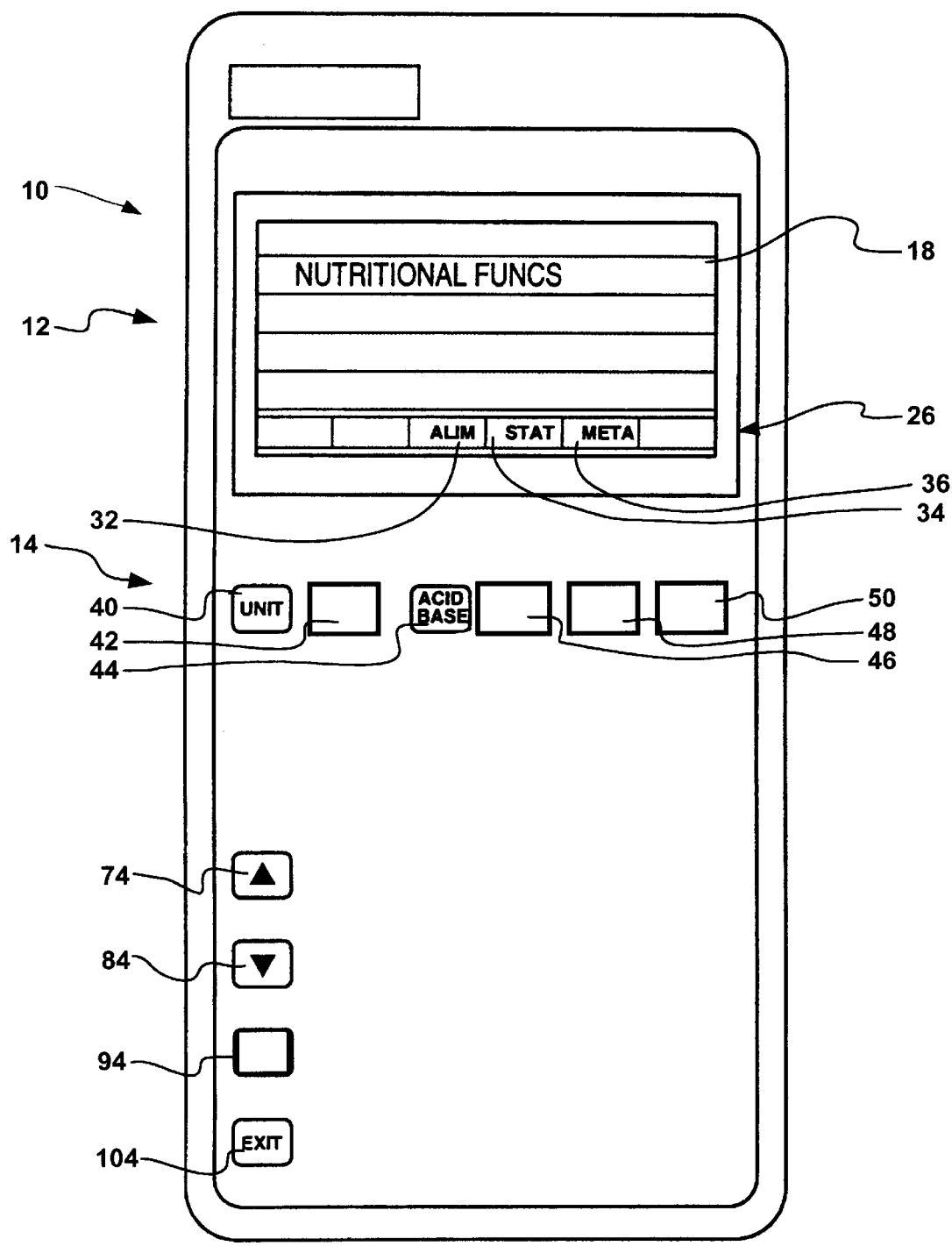
FIG. 41 is the portion of the device used for the nutritional functions.

Referring now to FIG. 41, therein is shown the device 10 with the screen 12 and the keypad 14 used for the nutritional functions numbered with the same numbers as in FIG. 1.

Figure 42:
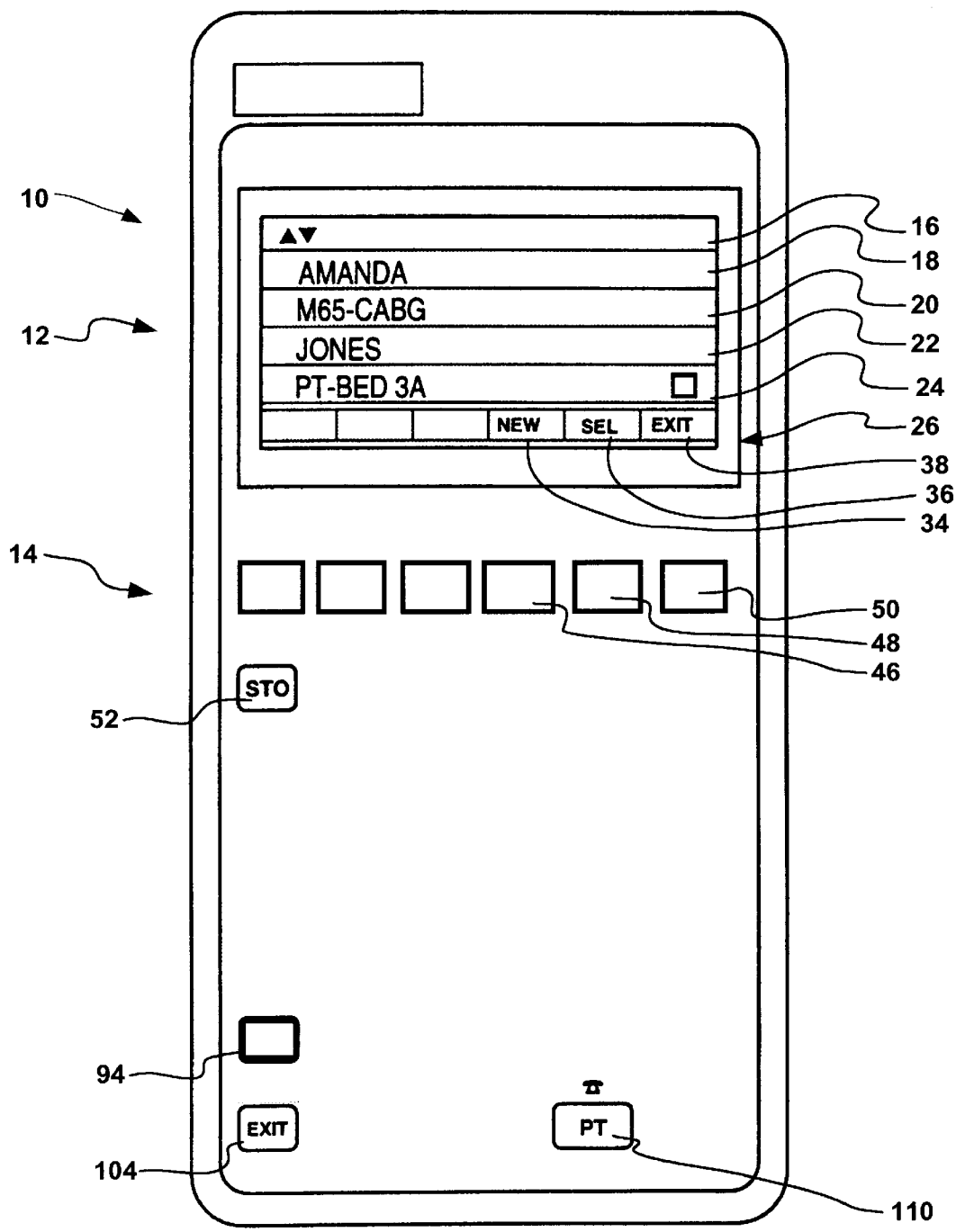
FIG. 42 is the portion of the device used for the patient logging and telephone numbers functions.

Referring now to FIG. 42, therein is shown the device 10 with the screen 12 and the keypad 14 used for the patient logging functions numbered with the same numbers as in FIG. 1.

Figure 43:
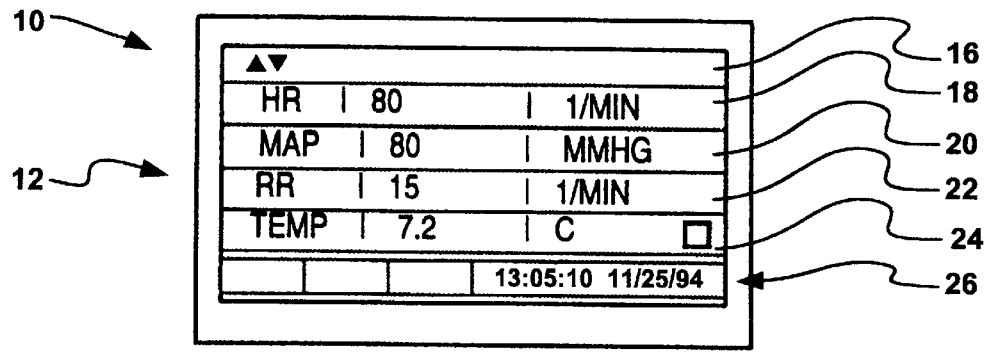
FIG. 43 is the screen resulting from another selection of the keys used for the patient logging.

Referring now to FIG. 43, therein is shown the screen 12 resulting from another selection of the keypad 14 used for the patient logging and telephone numbers functions numbered with the same numbers as in FIG. 1.

Figure 44:
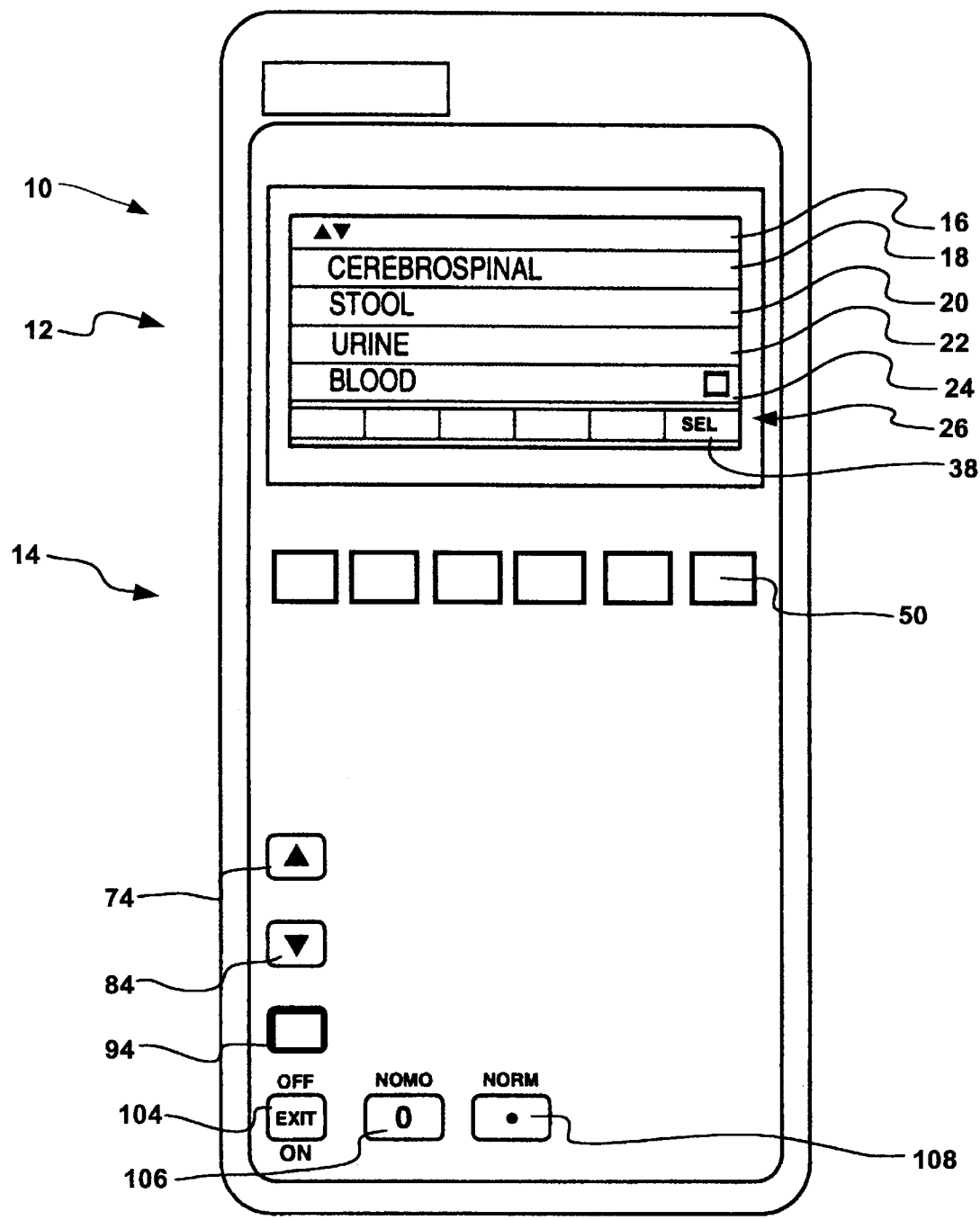
FIG. 44 is the portion of the device used for accessing the medical references which include tables of normal values and common nomograms.

Referring now to FIG. 44, therein is shown the device 10 with the screen 12 and the keypad 14 used for accessing the medical references numbered with the same numbers as in FIG. 1. The medical references include tables of normal values and common nomograms.

Figure 45:
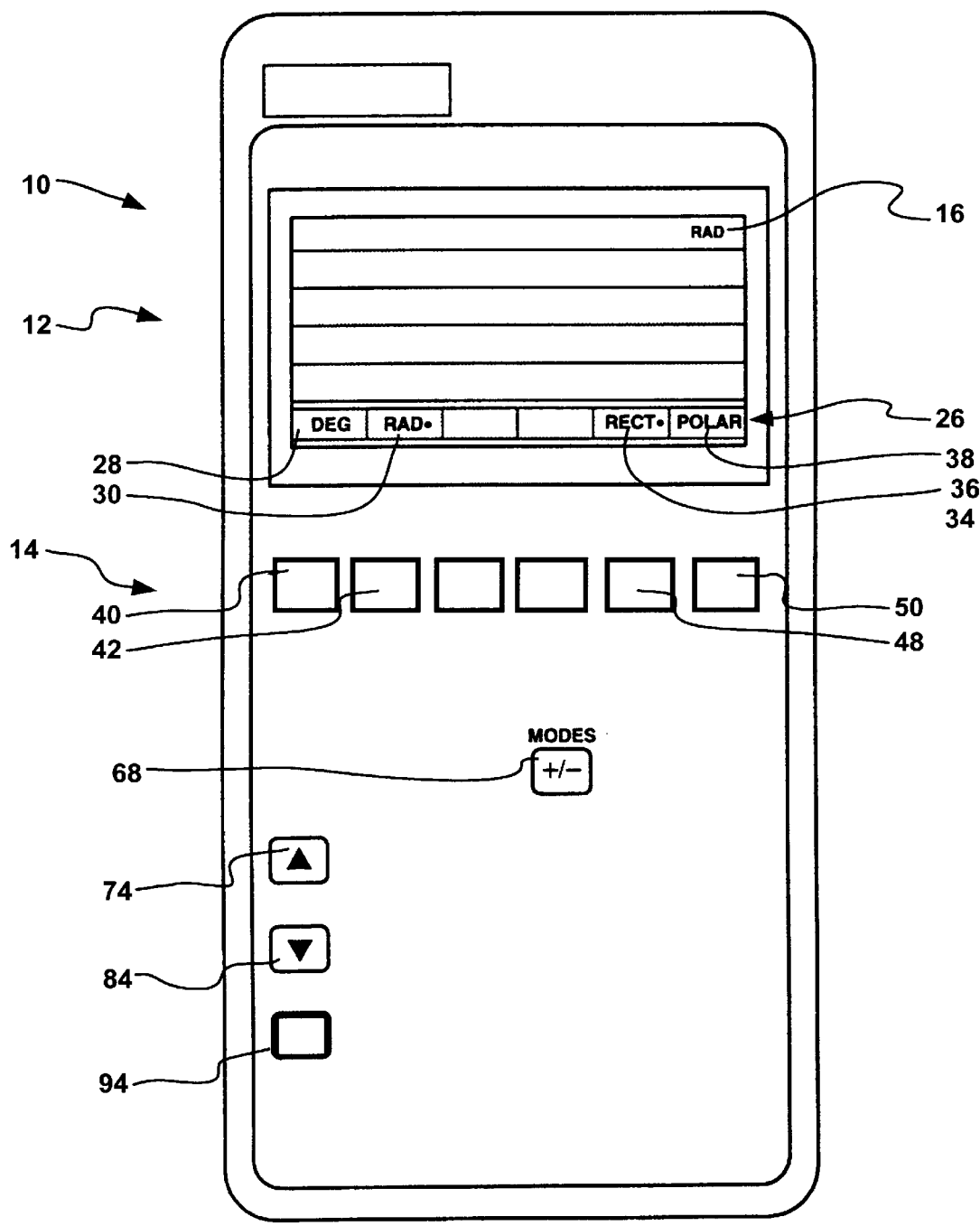
FIG. 45 is the portion of the device used for controlling the calculator modes functions.

Referring now to FIG. 45, therein is shown the device 10 with the screen 12 and the keypad 14 used for controlling the modes functions numbered with the same numbers as in FIG. 1.

Figure 46:
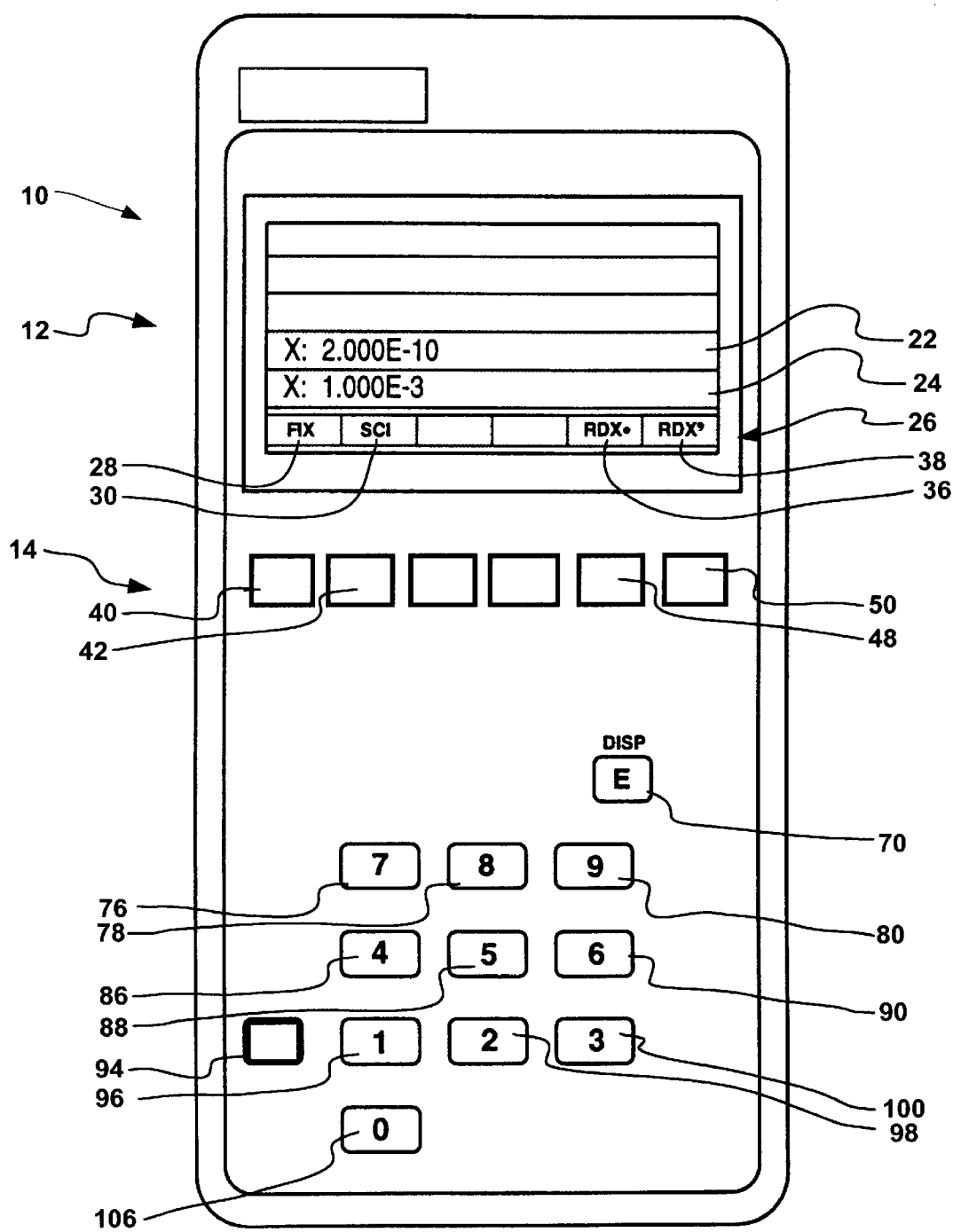
FIG. 46 is the portion of the device used for controlling the display format on the screen.

Referring now to FIG. 46, therein is shown the device 10 with the screen 12 and the keypad 14 used for controlling the display format on the screen 12 numbered with the same numbers as in FIG. 1.

Figure 47:
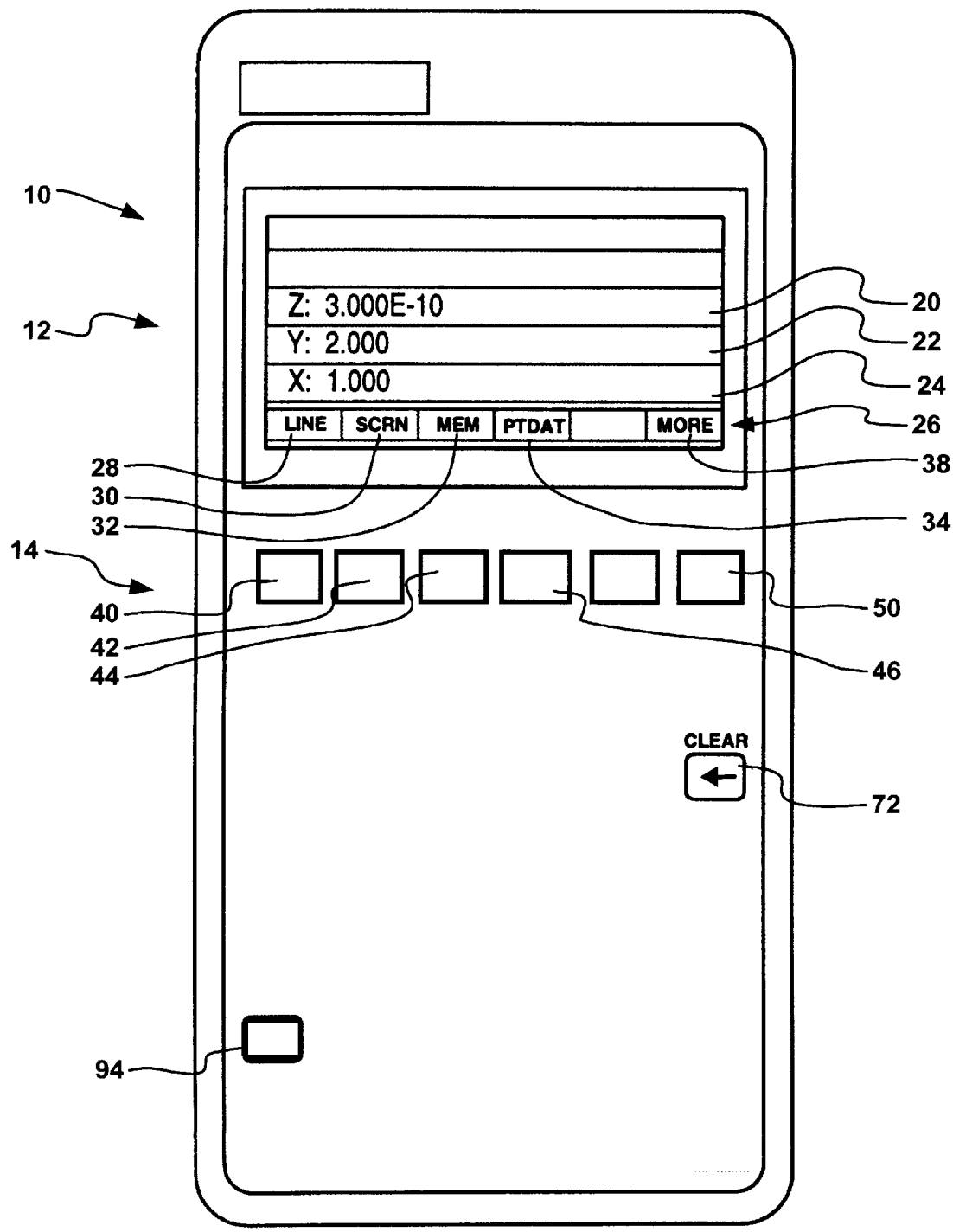
FIG. 47 is the portion of the device used for clearing selected parts of the screen.

Referring now to FIG. 47, therein is shown the device 10 with the screen 12 and the keypad 14 used for clearing selected parts of the screen 12 numbered with the same numbers as in FIG. 1.

Figure 48:
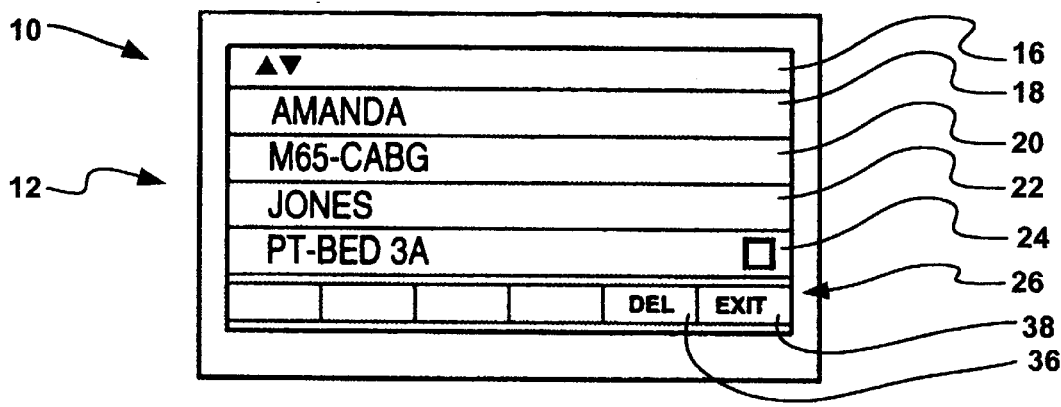
FIG. 48 is the screen resulting from another selection of the keys used for obtaining a list of patients.

Referring now to FIG. 48, therein is shown the screen 12 resulting from another selection of the keypad 14 used for obtaining a list of patients numbered with the same numbers as in FIG. 1.

Figure 49:
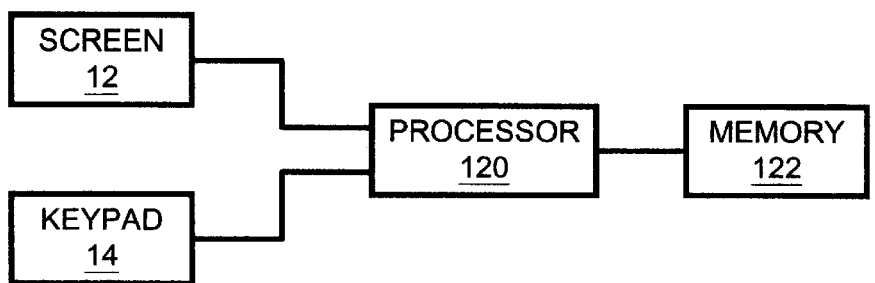
FIG. 49 is a simplified block diagram of the device.

Referring now to FIG. 49, therein is shown a simplified block diagram of the device 10 which includes the keypad 14, a processor 120, and a memory 122.

The operation of the device 10 is as follows.

Basic Mathematical Calculator

The mathematical section of the keyboard shown of FIG. 1 is similar to that of other mathematical calculators. The shift key ■ 94 gives choices above the selected key.

1. There is a conventional 10-key numerical pad for add, subtract, multiply, and divide functions.

2. Open and closed parentheses (■+ and ■−) keys 102 and 112 shifted give option of using the calculator in algebraic mode (e.g., 1+2=3), or in Reverse Polish Notation (RPN, e.g., 1, ENTER, 2, +) in the manner of most HP calculators. For doctors, nurses, and other health care workers, RPN may not be the first choice. Most may prefer conventional algebraic notation. The keys function as follows:

3. +/− key 68 changes sign of entries (in RPN). The E key 70 enters exponents (e.g., 1.E−5).

4. % and π keys 92 and 82 shifted give percent and pi.

5. Selected mathematical functions are:

trigonometric functions (sine, cosine, and tangent) and inverses inverse exponentiation ($Y^x 10^x$, and $e^x$)

square and square root common and natural logarithms

6. X←→Y key permits switch of X and Y values in the display register.

7. Complex numbers and matrix mathematics can be performed with the scroll keys 74 and 84 unshifted (■▲ and ■▼). This permits easy entry of matrix data, inversion, determinate, transpose, and solution of simultaneous equations.

Other functions can be added. Note that all the numerical keys have no shifted functions, and are available for additional functions.

Time and Medical Time Functions

As shown in FIG. 3, the TIME key 66 shifted [■x←→y] obtains time functions for telling time, alarms, timing, and time-stamping of data (as for patient vital signs records). Selecting TIME brings the softkey choices:

1. SET permits setting of the current date, time, and day of week. (This function is shown on the screen 12 of FIG. 3). Pressing SET brings a new set of softkeys:

12H on the softkey display 28 with softkey 40 selects 12 hour display format, e.g. 11:00 pm instead of 23:00.

24H on the softkey display 30 with softkey 42 selects 24 hour display format, e.g. 23:00 instead of 11:00 pm.

MDY on the softkey display 32 with softkey 44 selects Month/Day/Year format for dates.

DMY on the softkey display 34 with softkey 46 selects Day/Month/Year format for dates.

DAY on the softkey display 36 with softkey 48 selects day of week. Pressing the DAY softkey 48 brings a new selection of softkeys as shown in FIG. 4 with the days of the week. Softkeys 40, 42, 44, 46, 48, and 50 under MO, TU, WE, TH, FR and MORE in softkey displays 28, 30, 32, 34, 36, and 38, respectively. Selecting softkey 50 under MORE display SA, SU, and NONE (for no day display) in softkey displays 28, 30, and 32 above softkeys 40, 42, and 44 (screen not shown).

The scroll keys 74 and 84 unshifted (▲ and ▼) allow the user to move the cursor to the line (time, date, day) for setting. Cursor position is indicated by the ■ in the current line. In an alternate embodiment, a softkey could be added here for a flag to set visible or hidden display of time on the top status line.

2. ALRM shown in FIG. 5 permits setting an alarm. There are two softkey choices. (1) SET prompts for an integer (0–9, for up to 9 alarms). (2) CLR clears alarms that the user has set. After entering the number, the SET display appears (similar to setting time, except that there is the message SETTING ALARM N, as shown in FIG. 5, and there are softkey choices—VIEW, LABEL, DAY and EXIT. The DAY choices in this mode are expanded to include an additional key for EVERY day, and a custom screen to select any combination of days.

The LABEL softkey 42 permits entry of a line of alphanumeric characters (up to 20) which is displayed when the alarm sounds. After pressing the LABEL softkey 42, the user gets a prompt for a label and a new set of softkeys for alphanumeric labeling as shown in FIG. 6.

The ▲▼ symbols in the status line display line 16 indicate the scroll keys 74 and 84 are active to select a new row of softkeys for other characters, including parentheses, and useful general and medical symbols. Number keys on main keypad are used for numerical entry. The ▲▼ keys 74 and 84 could also scroll to pre-set messages for selection by the user, for example "CHECK MEDS" or "CALL LAB".

Pressing EXIT key 104 sets the alarm and returns to main TIME functions.

The status line on display line 16 shows that alarms are set when the user is operating the device 10 in different modes.

3. TMR sets a timer as shown in FIG. 7. The user gets prompted for H:M:S to set a timed interval. New softkey choices are BEG (to start), STOP (to stop), and RESET keys.

4. STPW is a stopwatch as shown in FIG. 8 for timing events. The displays are like the TM R function except the stopwatch counts up (instead of down like the timer). There is also a SPLIT softkey 42 to record (and store in numbered sequence) split times. Using the scroll keys 74 and 84 unshifted permits viewing the accumulated split times.

Drug and Infusion Calculations

This mode, as shown in FIG. 9, permits calculation of patient doses and infusion rates from the doctor's prescription orders. The choice of any dimensional unit (ml, mcg, mg, etc.) can be selected to simplify entry and avoid dimensional conversions. After completing an entry, the setting can be stored (and labelled) for future use.

Pressing DRUG key 42 unshifted brings a calculation screen which shows all the variables needed. Orders (Rx), patient weight, drug concentration, and calculated dose. The formula is:

DOSE=(Rx·WGT)/CONC

Two new softkeys also appear:

1. BSAIWGT—toggle softkey 48 for using Body Surface Area or Weight for dosage calculation
2. RENAL—adjustments using softkey 50 for renal insufficiency.

The user can use the scroll keys 74 and 84 unshifted to select the current line for data entry. The dimensional units of the current line can be changed using the UNIT key 40 unshifted. Pressing UNIT key 40 unshifted:

blanks all but the current line (except for scrolling values)

creates a scroll (in inverse color) in the units column of the display with all the possible choices for units, e.g., mg, mcg, g, etc.

creates one new softkey 50 shown in FIG. 10, SEL for selecting the choice of unit.

The user uses the scroll keys 74 and 84 to scroll to find the desired unit (only dimensional consistent choices are shown) and presses SEL softkey 50 unshifted to return to the calculation screen shown in FIG. 9.

If the user toggles to BSA (instead of WGT) using the softkey 46, the user gets a screen for entering WGT and HGT (Height). BSA is calculated from known nomograms. (See Cardiac function section for formulae).

Infusion rate calculations are accessed by selecting INFUSE (■ DRUG) key 42 shifted. The function is identical to drug calculations except the order (Rx) has the units mass per patient weight per unit time (e.g. mg/kg/min), and DOSE (shown in FIG. 9, display line 24) has the units volume/time (e.g., ml/hr). Select new units in the same manner as drug calculations.

While in the DRUG or INFUSE screen, the user can store the current settings and recall the settings for future use (i.e. when using the same medication on patients with different weights or prescriptions). To Store the setting, press key 52 unshifted which is STO N, where N is a number 0–9, for ten allowed drug or infusion memory settings.

Figure 11:
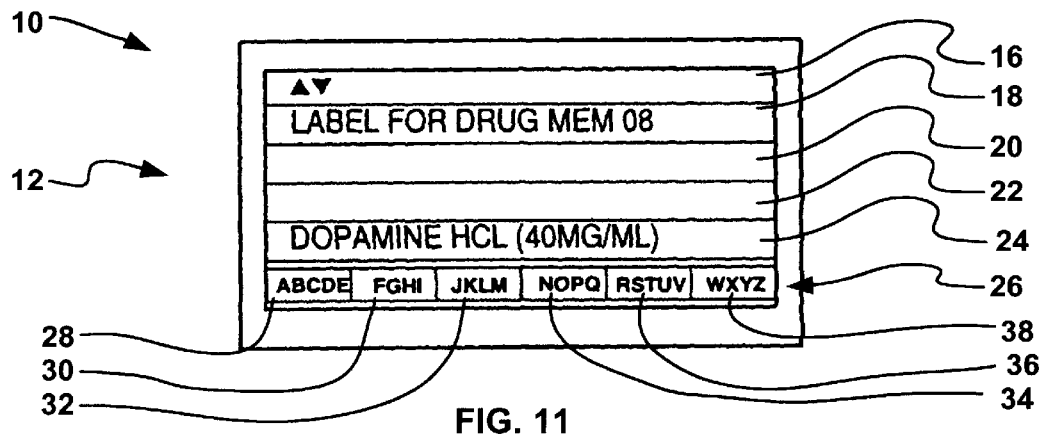
FIG. 11 is the screen resulting from another selection of the keys used for the drug and infusion calculation functions.

The user gets a prompt for a label and a new set of softkeys for alphanumeric labeling as shown in FIG. 11. As an alternative, the softkeys can be labeled with RX?, WGT, CONC, DOSE, etc. for direct input. Touching one of the softkeys selects the associated input and allows the input of data from the numerical keys. The cursor 24 will move to the appropriate location to indicate which associated input is selected.

The ▲▼ symbols in the status line, display line 16, indicate the scroll keys 74 and 84 are active to select a new row of softkeys for other characters, including parentheses, and useful general and medical symbols. Number keys on the keypad are used for numerical entry.

The user can recall the settings from memory with the RCL DRUG N or RCL INFUSE N command using RCL key 54 and DRUG or INFUSE key 42 unshifted or shifted, respectively. If the user has entered a label for this setting, then the label will appear in the place of softkeys 44 and 46 in the calculation display screen 12.

If the user gives no number choice for memory, i.e., RCL DRUG or RCL INFUSE, then the screen displays a list of the labels of the stored settings. The user can scroll and select choice.

The RENAL softkey 46 in FIG. 9 is an option that permits the user to adjust the dose of common drugs for patients with renal insufficiency. Pressing RENAL softkey 46 clears the DOSE/RATE display and gives a screen 12 for creatine clearance CREA on display line 22, the drug used on line 22, DRUG, and the fraction for dose reduction on line 20.

Pressing DRUG key 42 in the RENAL screen allows the user to scroll to choices of common drugs (a better entry system, such as letter entry with word completion is another alternative as shown in FIG. 12). Selecting a drug returns to the display shown in FIG. 13 and displays the fraction for reduction.

Values for dose correction are found in *Clinical Nephrology* 7:81 (1977). A partial list of drugs accessible on the screen 12 of FIG. 14 is:

| | | |
|---|---|---|
| Acyclovir | Cephradine | Minocycline |
| Amantadine | Chloramphenicol | Moxalactam |
| Amikacin | Clindamycin | Nafcillin |
| Amoxicillin | Cloxacillin | Netilmicin |
| AmphotericinB | Colistamethate | Oxacillin |
| Ampicillin | Dicloxacillin | PenicillinG |
| Azlocillin | Doxycycline | Piperacillin |
| Bactrim/Septra | Erythromycin | PolymixinB |
| Carbenicillin | Ethambutol | Rifampin |
| Cefaclor | Flucytosine | Streptomycin |
| Cefamandole | Gentamicin | Sulfisoxazole |
| Cefazolin | Isoniazid | Thiabendazole |
| Cefoperazone | Kanamycin | Ticarcillin |
| Cefotaxime | Ketoconazole | Tobramycin |
| Cefoxitin | Methicillin | Trimethoprim |

-continued

| Cephalexin | Metronidazole | Vancomycin |
| Cephalothin | Mezlocillin | |
| Cephapirin | Miconazole | |

Cardiac and Hemodynamic Function Calculations

This function, as shown in FIG. 15, permits calculation of the many measures and indices that describe cardiac function. Many of the measures use common input values—body surface area, measured pressures, etc. Once entered, these values are shared among all the measures that use them, so the user does not need to re-enter data for different calculations. The CARD♥ key 56 unshifted has three sofikeys for evaluating the different cardiac functions, and one key for reviewing (or inputting) patient data.

When the user selects a function or index to evaluate, the user receives prompts for the necessary input data, and the function is evaluated. The input parameters are stored for use in future calculations because many cardiac functions have the same parameters as independent variables. Thus, the user need not repeat entries.

Values of cardiac function tests are found by scrolling through lists of functions. Displayed values are divided into three groups for easy access, in addition to patient data:

1. ♥FNC—cardiac function tests starting with the screen 12 shown in FIG. 16. Values include:

CO, cardiac output (Fick or physiologic)
CI, cardiac index (CO/BSA)
SV, stroke volume (CO/HR)
SVI, stroke volume index (CI/BSA)
EF, ejection fraction (SV/EDV)
BVI, blood volume index
CBVI, central blood volume index Calculation of cardiac index is shown on the screen 12 in FIG. 16 after softkey 46 has been pressed under CARD in the softkey display 34. In this case, the user must input the parameters which can determine the cardiac output (CO), and the patient body surface area (BSA). After pressing CO, the user gets a screen with these two variables. Scrolling to the line, the user can either enter a value directly, or select the parameter.

Selecting the parameter brings screen 12 of FIG. 17 to calculate the parameter from other independent variables.

Selecting BSA prompts for patient height HGT and weight WGT. If not entering CO directly, selecting CO gets a screen for determining CO by the Fick Equation, $CO = \dot{V}_{O_2}/8.5(CaO_2 - C\bar{v}O2)$, where $CaO2 = 1.36(Hgb)(SaO2) + 0.003 PaO2$, and $C\bar{v}O2 = 1.36(Hgb)(Sp\ \bar{v}O2) + 0.003 PaO2$.

The result of the above equations are displayed on the screen 12 shown in FIG. 18. Other methods of determining CO may be an option for the CO screen. Again, once the basic parameters are entered, they are saved for other functions.

2. WORK—cardiac work indices as displayed on the screen 12 shown in FIG. 19.

LCWI, left cardiac work index
LCWI=CI·MAP·0.0136
LVSWI, left ventricular stroke work index
LVSWI=SI·(MAP−PAWP)·0.0136
RCWI, right cardiac work index
RCWI=CI·MPAP·0.0136
RVSWI, right ventricular stroke work index
RVSWI=SI·MPAP·0.0136

3. RESIS—vascular resistances as displayed on the screen 12 shown in FIG. 20.

SVR, systemic vascular resistance
SVR=(MAP−CVP)·79.92/(CO)
SVRI, systemic vascular resistance index
SVRI=(MAP−CVP)·79.92/(CI)
PVR, pulmonary vascular resistance
PVR=(MPAP−PAWP)·79.92/(CO)
PVRI, pulmon. vascular resistance index
PVRI=(MPAP−PAWP)·79.92/(CI)

The above vascular resistances are displayed on the screen 12 in FIG. 20.

DATA—For data entry from DATA on the softkey display 32 and softkey 44, the softkeys are:

a) PT—patient data. Pressing PT gives a new menu for HGT and WGT as shown in FIG. 21. A display of BSA also appears. Initial value of BSA is calculated using the algorithm:
$BSA = (HGT)^{0.425} \cdot (WGT)^{0.725} \cdot 0.007184$
(BSA in $m^2$, HGT in cm, WGT in kg).

BSA can be entered independently by scrolling to BSA and entering a value. This value is retained for calculations. The Ideal Body Weight estimates are here.

Pressing the UNIT key 40 unshifted allows the user to select new dimensional units in the same manner as for the drug calculations.

b) PRES—pressure data. PRESS gives six data lines of which four are visible as shown in FIG. 22 for different pressures. The scroll keys 74 snd 84 are used to select and enter data.
CVP, central venous pressure
SP, systolic pressure
DP, diastolic pressure
MAP, mean arterial pressure. If no value is given, the MAP value is calculated from the SP and DP data by MAP=(SP+2 DP)/3, and marked as estimate with *.
MPAP, mean pulmonary artery pressure
PAWP, pulmonary artery wedge pressure Default units are mmHg, but the user can use the UNIT key 40 unshifted to select new units for each entry. Any calculations using these values adjusts the units appropriately.

c) BLOOD—blood data. BLOOD gives six data lines of which four are visible as shown in FIG. 23 for different blood parameters. The scroll keys 74 and 84 are used to select and enter data.
SAO2, arterial oxygen saturation
SVO2, mixed venous oxygen saturation
HGB, blood hemoglobin
HCT, blood hematocrit
PVOL, blood plasma volume
PAO2, arterial $O_2$ partial pressure As always, the user can use the UNIT key 40 unshifted to select new units for each entry. Any calculations using these values adjusts the units appropriately.

d) HEART—heart data. HEART gives four data lines for heart parameters as shown on screen 12 of FIG. 24. The scroll keys 74 and 84 are used and data entered.
CO, cardiac output. If CO is not entered, then, CO is calculated using the Fick equation,
$CO = \dot{V}O2/8.5(CaO_2 - C\bar{v}O2)$, where
$CaO2 = 1.36(Hgb)(SaO2) + 0.003 PaO2$, and
$C\bar{v}O2 = 1.36(Hgb)(S\bar{v}O2) + 0.003 PaO2$.

MTT, mean transit time
EDV, end diastolic volume
ESV, end systolic volume

Use the UNIT key 40 unshifted to select new units for each entry. Any calculations using these values adjusts the units appropriately.

Respiratory and Ventilatory Calculations

These functions evaluate respiratory and ventilatory parameters as shown on the device 10 in FIG. 25. In the same manner as for the cardiac functions, the user can access a parameter to evaluate (such as VC, vital capacity) and get a screen that prompts for the needed variables. Once the variables are entered they are stored as patient data and are used for other calculations.

The softkey displays 30, 32, and 34 with softkeys 42, 44, and 46 are respectively VENT for determining ventilation parameters, VOL for finding vital capacity and noting the different lung volumes (from pulmonary tests), and DATA for the patient data.

Descriptions of the function keys:

1. VENT softkey 46 in FIG. 25—ventilation parameters as shown on screen 12 of FIG. 26. There are prompts for patient data, and computation of minute ventilation (MV), tidal volume (TV), and respiration rate (RESP) from the Radford nomogram. In this screen the user can enter the inspired:expired ratio (I:E) and calculate the required flow rate.

Scrolling to a variable and choosing SEL softkey 48 gives data screens (same as pressing the DATA key) as shown of screen 12 of FIG. 27. The first screen is for HGT, WGT, and SEX (key prompts for MIF). A display of BSA also appears. Initial value of BSA is calculated using the algorithm:

$BSA = (HGT)^{0.425} \times (WGT)^{0.725} \times 0.007184$ (BSA in $m^2$, HGT in cm, WGT in kg).

BSA can be entered independently by scrolling to BSA and entering a value. This value is retained for calculations. The user can scroll to estimates of Ideal Body Weight (IBW).

Pressing the UNIT key 40 unshifted allows the user to select new dimensional units in the same manner as for the drug calculations.

The softkey 50 for MORE allows entry of other optional data as shown on screen 12 in FIG. 28:

FEVT—fever temperature
ALT—altitude
INTB—intubation flag (Y/N)
DSPC—dead space
COMA—coma flag (Y/N)
AGE—age of patient These data are used to correct the predicted tidal volumes, if desired.

The useful formulae are:

MV (1pm) = BSA ($m^2$) × $F_{sex}$
where $F_{sex}$ = 4.0 (men), 3.5 (women)
TV (ml) = IBW (kg) × 2(ml/kg)
where IBW is ideal body weight,
$IBW_{men}(kg) = HGT^2(m) \times 23$
$IBW_{women}(kg) = HGT^2(m) \times 21.5$ There are corrections for tidal volume:
a) not in coma, add 10%
b) Fever: add 9% every degree above 37° C. (rectal)
c) Altitude: add 5% each 2000 ft above sea level (or 8% every 1000 m)
d) Intubation: subtract volume equal to weight in kg (½ weight in lbs)
e) Dead Space: add equipment dead space.

2. VOL softkey 48 in FIG. 25—volumes. The first screen 12 in FIG. 29 is a display showing the relationship of lung volumes. There is a softkey for calculating vital capacity, VC by the following formulae (VC in ml, age in years, height in cm):

$VC_{women} = (27.63) - (0.112 \cdot AGE)) \cdot HGT$
$VC_{men} = (21.78) - (0.101 \cdot AGE) \cdot HGT$ The user can scroll to the different lung volumes on the screen 12 in FIG. 29 and enter values, from which others are calculated according to the relationships shown on the VOL screen. Any known value is shown in inverse in the softkey display 26.

3. DATA softkey 44 in FIG. 25—for patient data. The screens are the same as those shown for data entry in the VENT functions. Data can be entered here, in DATA mode, or in the function screens (VENT and VOL). All data are retained for other calculations that require them. If not erased, the data are also available to other functions, such as the CARD functions, which use common variables, such as patient height or weight.

Acid-Base Calculations

The acid-base functions shown for the device 10 in FIG. 30 (1) permit calculations with all the usual acid-base equations (Henderson-Hasselbach, Kassirer-Bleich, etc),(2) show a list of A-B disorders and expected compensations, and (3) permit calculation of the usual deficits and osmolality, etc.

The corresponding softkey displays 32, 34, and 36 for softkeys 44, 46, and 48 are respectively AB-EQ, DIS, and IONS.

1. AB-EQ—Acid-Base basic equations.

The choices, as shown in the screen 12 of FIG. 31, are for (1) the Henderson-Has-selbach equation, (2) the Kaiser-Bleich equation, (3) relation of pH and H+, and (4) arterial blood gas functions.

As always, independent variables are saved after they are entered for use in other calculations.

For the Henderson-Hasselbach equations, which use the following formulas, the data is prompted by the screen 12 in FIG. 32:

$$pH = 6.1 + \log \frac{[HCO_3^-]}{PaCo_2 \cdot \alpha \cdot 0.0301} \quad \text{or,}$$

$$pH = pK + \frac{[HCO_3^-]}{[H_2CO_3]}$$

The user can toggle between the H2CO3 or the PACO2 formulations with the softkey, to accept either type of input.

The screen 12 in FIG. 33 for the Kassirer-Bleich equation is similar to the H-H equation screen, except that the three variables are $H^+$, $PCO_2$, and $HCO_3^-$. The formula is:

$H^+ = 24 \cdot \log(PCO_2/[HCO_3^-])$

The relation between $H^+$ and pH is found the next screen choice. The user can scroll between the pH values and view the $H^+$. There is a key for temperature correction here. Selecting TEMP allows entering a temperature and automatically corrects the pH value (default is 37° C.). (For the pH vs. H+ calculation the "0.8/1.25" rule is used. This has the formula (H+ in nEq/L):

$$H^+ = 40 \cdot (1.25)^{[10 \cdot (7.4 - pH)]}$$

The last AB-EQ function, as shown on the screen 12 in FIG. 34, gives the corrections for arterial blood gases as a function of temperature. If the temperature has already been entered it is used here and need not be entered. The user can toggle between the measured values or the correction factors. Uncorrected and corrected values are differentiated by a *. The USE? softkey 44 asks to apply (use) or un-apply the correction factors to entered ABG data. Approximate correction equations are found in *J Am Coll Emerg Physicians* 8:247 (1979).

2. Acid-Base Disorders, DIS, as shown on screen 12 in FIG. 35. This menu identifies simple acid-base disorders and indicates initial changes and expected compensation. The six states (other than normal) are:

metabolic acidosis metabolic alkalosis respiratory acidosis, acute respiratory acidosis, chronic respiratory alkalosis, acute respiratory alkalosis, chronic The screen 12 in FIG. 35 has two softkey display choices, SHOW or FIND.

Scrolling to the selected disorder and choosing the SHOW softkey 48 gives principal facts about the disorder on the screen 12 in FIG. 36. The second screen shown in FIG. 37 is accessed by pressing the NEXT softkey 50. The BACK softkey 48 under the softkey display 26 in FIG. 37 returns to the first screen of FIG. 36.

Selecting the FIND softkey 50 under the softkey display 26 in FIG. 35 prompts for ABG values pH or H$^+$, and PCO$_2$, or HCO$_{3-}$ from the DIG screen. From the proper set independent values, the device 10 identifies the acid-base state of the patient according to the well-know relations shown in FIG. 38 (*JAMA*, 223:3 1973). This acid-base mapping shown in FIG. 38 could also be displayed on a high resolution screen 12. Actual values can be found using the screen 12 in FIG. 39.

Choosing RX? softkey 48 under the softkey display 36 offers the clinician a recommended prescription, such as giving a suggested amount of bicarbonate, or adjusting PCO$_2$.

Thus by inputting a diagnosis, the device 10 outpus a recommended treatment or course of action.

3. IONS as shown in screen 12 of FIG. 40—simple formulae for calculation of other acid-base related quantities. There are five choices:

AG: anion gap (in mEq/L):
   AG=Na$^+$-Cl$^-$+HCO$_3^-$

HCO$_{3-}$, Deficit (in mEq/L):
   HCO$_3^-$,def=[WGT]·0.4·(des, HCO$_3$-meas, HCO$_3^-$)

BE, base excess (in mEq/L):
   BE=(1−0.014Hgb)×[(HCO$_3^-$−24)+(9.5+1.63Hgb)(pH−7.4)]

OSM,S, serum osmolality (mOsmol/kg) where Na$^+$ and K$^+$ are in mEq/L, Glucose and Urea in mg/dL.

$$Osm, S = 2(Na^+ + K^+) + \frac{Glucose}{18} + \frac{Urea}{2.8}$$

XL, Lactate, excess (mmol/L)

$$XL = (L_t - L_n) - (P_t - P_n)\frac{L_n}{P_n}$$

($L_n$ and $P_n$ are normal values, 1.0 and 0.1 mmol/L, resp.)

Choosing these functions from the screen gives a screen 12 in FIG. 40 that prompts for the given independent variables, as shown in the equations. As always, the user can select choice of units. Also, if these values have been entered previously, they will appear in the displays as defaults.

Nutritional Functions

The NUTR functions as shown in the computer 10 of FIG. 41 evaluate nutritional status, metabolic functions, calculations for hyperalimentation, and some special functions.

1. META softkey display 36 selection gives choice of calculating:

BMR, basal metabolic rate (kcal/m$^2$/hr)
   BMR=37−[AGE(yrs)−20]/10

BEE, basal energy expenditure (Harris-Benedict equations, in kcal/hr)
   BEE$_{Male}$=66+13.7WGT+5Hgt−6.8Age
   BEE$_{Female}$=655+9.6Wgt+1.8Hgt−4.7Age
      where for the BEE equations, Wgt is weight in Kg, Hgt is height in cm, Age in years.

The screens and prompts are similar to screens shown earlier with lines for the independent variables and the function result.

2. STAT softkey display 34 selection gives nutritional status (assessment). Choices include:

NB, nitrogen balance (g)

BUN/Urea conversion
   BUN=Urea /2.14

LBM, lean body mass (kg)
   LBM=7.138+0.02908(Cr)$_{mgUrine}$,24 hr

IBW, ideal body weight (kg)
   IBW$_{male}$=[Hgt(m)]$^2$·23
   IBW$_{Female}$=[Hgt(m)]$^2$·21.5

3. ALIM softkey display 32—for hyperalimentation. In these calculations, the user determines the caloric and nutrient intake, and fluid requirements of a patient. (This may depend on the diagnosis and patient condition). Then, the user determines the time, concentrations, and flow rate for the nutrients. The calculations are a combination of caloric and fluid calculations, and infusion calculations already mentioned. This function is very useful.

Patient Logging and ☏ Key

These functions are shown on the computer 10 in FIG. 42. The PT key 110 unshifted allows the user to start a log of vital signs data for a patient. Pressing PT key 110 gets the screen 12 where the user can (1) enter a new patient name, or (2) scroll through a list of existing patient files and select an existing patient.

If NEW softkey 46 is selected, then the user gets the usual labeling screen with prompt for alphanumeric input, then a data input screen. Choosing an existing name gets the data input screen directly. The data screen 12 shown in FIG. 43 allows the logging of four vital signs:

HR, heart rate

MAP, mean arterial blood pressure

RR, respiratory rate

TEMP. temperature

Current time is shown in the softkey line. Pressing STO key 52 saves the data and logs the current time. The user can scroll through earlier entries with the scroll keys.

The ☏ key 110 shifted permits the user to store telephone data in an alphabetized directory. Pressing ☏ key 110 gives a phone list, and the option to enter new numbers in the standard manner. Alphabetization is automatic.

Tables Of Normal Values And Common Nomograms

The NORM key 108 shifted, shown on the device 10 in FIG. 44, accesses a vast amount data of "normal values". These data are divided by function and include normal values for:

1. Blood chemistry (chemical)
2. Hematology (with age functions, lists of "Cytes", bone marrow data, and chemical data)
3. Urine and urinalysis
4. Stool
5. Cerebrospinal fluid
6. Pleural fluid
7. Ascitic fluid
8. Gastric fluid
9. Synovial fluid
10. Semem analysis
11. Other miscellaneous (breath, sweat, etc.)
12. Cardiac function test results
13. ECG wave amplitudes
14. Echocardiography data
15. Pulmonary function test data (lung volumes, ventilation, hemodynamics, gases, breathing mechanics)
16. Renal function
17. Endocrine function and hormones
18. Normal solutions and salts.

The user gets a scroll screen of these topics. After selecting a topic, the user can scroll through values.

A typical source of such values are pocket-size handbooks, such as *Medi-Data's Normal Values,* published by the Rodram Corp 1988, Mexico City, or *Facts and Formulas,* compiled by R. C. Rollings, M.D. 1985, publ. by McNaughton and Gunn.

Selecting NOMO key 106 shifted gives a scrolling menu of common useful nomograms, formulae, and data including:

toxicity (e.g., acetaminophen and salicylate poisoning)

burn fluid replacement gas bottle info (capacities, duration, and factors)

neutral thermal environment temperature, T=f(weight, age)

fetal age estimation (e.g., from OB ultrasound measurements)

Modes

Pressing the MODES key 68 shifted[■ (+/−)], on the device 10 shown in FIG. 45, brings up the softkeys selection in the softkey displays 28, 30, 36, and 38.

Choices are:

1. Degrees or radians for angular calculations.

2. Rectangular or polar coordinates. Selecting POLAR converts the current X and Y values to polar coordinates [X register $R=\rightarrow(x^2+y^2)^{1/2}$, and Y register $\theta=atan(y/x)$]. Selecting RECT coverts back to rectangular coordinates by using the inverse formulas.

3. An indicator note appears in the top display line 16 of the screen 12 to indicate current mode choice (if unconventional, e.g., RAD) so that the user will not be confused about the current setting.

4. Scroll keys 74 and 84 could be used to select other modes, if needed.

Displays

Selecting the DISP key 70 shifted [■ E] on the device 10 in FIG. 46 permits control of the display format on the screen.

The choices are:

1. FIX softkey 40 for fixed notation, e.g., FIX 3 ENTER gives display 1.000, FIX 6 ENTER gives display 1.000000, etc. Softkey display disappears from screen after selecting ENTER.

2. SCI softkey 42 for scientific notation, e.g., SCI 3 ENTER gives display 1,000E-3, FIX 6 ENTER gives display 1.000000E-3, etc. Soft function line (bottom display line) disappears from screen after selecting ENTER.

3. RDX. softkey 48 selects period (.) for decimal radix and comma (,) for thousands delineation, e.g., 1,000.000.

4. RDX' softkey 50 selects comma (,) for decimal radix and period (.) for thousands delineation, e.g., 1.000,000 (as in European countries).

Other choices are possible by replacing the two unused softkeys (between FIX/SCI and RDX choices) with scroll keys.

Clear

The CLEAR key 72 shifted in the device 10 shown in FIG. 47 permits clearing of selected parts of the screen 12.

Use of the unshifted arrow [←] erases the last digit on the current entry, e.g. 3.1418, gives 3.141. The user can repeat the ← key to continue erases (backspacing) over single digits until the entire line is erased.

Use of the CLEAR key 72 shifted [■←] obtains a menu of other erasing modes. The respective softkey 28, 30, 32, 34, and 38 selections are:

1. LINE which erases the entire current line, e.g., the X value (in math mode) or the current function line (when in one of the function modes, such as DRUG).

2. SCRN which erases the values from the entire screen. In a function mode, the function remains on the screen, and only the values are erased, leaving the screen ready for a new entry.

3. MEM which clears the values stored in the memory stack (from the STO command for single values).

4. PTDAT which clears all data values currently in the data calculation memories (weight, pressures, etc.).

5. MORE which obtains a new set of softkeys to clear other stored items. The new softkeys are:

a. DRUG—which then brings a list of the stored DRUG programs onto the screen, and a new CLR softkey. Use the scroll keys to select the drug program to clear, then press CLR. If the user has labeled the programs the labels appear in the list to make the selection easier.

b. INFUS—same manner as DRUG above, but for infusion programs.

c. PT—same manner as DRUG above, but for records of vital signs for patients. When PT is pressed, a labelled list of current patients appears for selection.

The functions under the MORE softkey 50 could also have a print function if the user has a printer.

While the invention has been described in conjunction with a specific best mode, it is to be understood that many alternatives, modifications, and variations will be apparent to those skilled in the art in light of the aforegoing description. There are many ways of implementing the present invention electronically based on the above description as would be evident to those skilled in the art. Different types of microprocessors, embedded processors, and application specific integrated circuits could be used with associated memory to implement the above invention. Accordingly, it is intended to embrace all such alternatives, modifications, and variations which fall within the spirit and scope of the included claims. All matters set forth herein or shown in the accompanying drawings are to be interpreted in an illustrative and non-limiting sense.

What is claimed is:

1. A handheld medical device, comprising:

an output mechanism for outputting a plurality of preconfigured prompts and a medical answer;

an input mechanism operatively associated with said output mechanism, said input mechanism for inputting a predetermined medical question, information, and choices among plurality of said preconfigured prompts;

memory operatively connected to said input and output mechanisms, said memory containing said plurality of preconfigured prompts for said predetermined medical question and said medical answer; and a processor connected to said memory and said input and output mechanisms, said processor:

responsive to said predetermined medical question input at said input mechanism to cause said memory to provide said preconfigured prompts to said output mechanism, responsive to said preconfigured prompts to receive said information and said choices among said plurality of preconfigured prompts from said input mechanism, responsive to said choices among said plurality of preconfigured prompts to process said medical answer, and operable with said memory as a result of said predetermined medical question, said information, and said choices among said plurality of preconfigured prompts to provide said medical answer to said output mechanism.

2. The handheld medical device as claimed in claim 1 wherein:

said output mechanism is capable of outputting a plurality of preconfigured prompts and a plurality of information adjacent to and related to said plurality of preconfigured prompts, said output mechanism is capable of outputting at least one preconfigured prompt related to said predetermined medical question;

said input mechanism is capable of being operatively associated with said output mechanism and said at least one preconfigured prompt; and said processor is operable to establish the operative association of said input mechanism with said at least one preconfigured prompt from said output mechanism.

3. The handheld medical device as claimed in claim 1 wherein:

said output mechanism is a display capable of displaying a plurality of preconfigured prompts and a plurality of information adjacent to and related to said plurality of preconfigured prompts, and said display is capable of simultaneously displaying all of said preconfigured prompts and input information related to said predetermined medical question.

4. The handheld medical device as claimed in claim 1 wherein:

said memory contains drug dosage information;

said processor includes a calculator;

said processor is responsive to said input mechanism inputting a drug question to provide said preconfigured prompt to obtain patient information;

said processor is responsive to said input mechanism inputting patient information to use said patient information and said drug information from said memory to calculate a drug dosage answer; and said processor is operable to cause said output mechanism to output said drug dosage answer.

5. The handheld medical device as claimed in claim 1 wherein:

said memory contains respiratory and pulmonary information;

said processor includes a calculator;

said processor is responsive to said input mechanism inputting a respiratory or pulmonary question to provide said preconfigured prompt to obtain prescription and patient information;

said processor is responsive to said input mechanism inputting prescription and patient information to use said prescription and patient information and said respiratory and pulmon ary information from said memory to respectively calculate a respiratory or pulmonary answer; and said processor is operable to cause said output mechanism to output said respiratory or pulmonary answer.

6. The handheld medical device as claimed in claim 1 wherein:

said memory contains acid-base information and an acid-base nomogram;

said processor includes a calculator;

said processor is responsive to said input mechanism inputting an acid-base question to use said acid-base information and said acid-base nomogram from said memory to calculate an acid-base answer; and said processor is operable to cause said output mechanism to output said acid-base answer.

7. The handheld medical device as claimed in claim 1 wherein:

said memory contains a medicai mapping and a medical nomogram;

said output mechanism is a display capable of displaying said medical mapping and said medica nomogram;

said processor is responsive to said input mechanism inputting a medical mapping question or medical nomogram question to cause said output mechanism to respectively display said medical mapping, or said medical nomogram.

8. The handheld medical device as claimed in claim 1 wherein:

said memory contains information on normal values for various human conditions; and said processor is responsive to said input mechanism inputting a question on a normal human condition to use said information from said memory to provide said normal value and to cause said output mechanism to output said normal value as an answer.

9. The handheld medical device as claimed in claim 1 wherein:

said memory contains cardiac and hemodynamic information;

said processor includes a calculator;

said processor is responsive to said input mechanism inputting a cardiac or hemodynamic question to use said cardiac and hemodynamic information from said memory to respectively calculate a cardiac or hemodynamic answer; and said processor is operable to cause said output mechanism to output said cardiac or hemodynamic answer.

10. The handheld medical device as claimed in claim 1 wherein:

said memory contains nutrition information;

said processor includes a calculator;

said processor is responsive to said input mechanism inputting a nutrition question to provide said preconfigured prompt to obtain patient information;

said processor is responsive to said input mechanism inputting patient information to use said patient information and said nutrition information from said memory to respectively calculate a nutrition answer; and said processor is operable to cause said output mechanism to output said nutrition answer.

11. The handheld medical device as claimed in claim 1 wherein:

said input information is patient information;

said memory is capable of storing said patient information; and said processor is responsive to said input mechanism inputting said predetermined medical question to cause said output mechanism to output said patient information.

12. A handheld medical calculator and reference device, comprising:

a display for outputting first and second preconfigured prompts and a medical answer;

a keypad operatively associated with said display, said keypad for inputting a predetermined medical question, information, and choices among said first and second preconfigured prompts;

a memory operatively connected to said keypad and display, said memory containing said first and second preconfigured prompts for said predetermined medical question and medical data; and a processor connected to said memory and said keypad and said display, said processor:

responsive to said predetermined medical question input at said keypad to cause said memory to provide said first preconfigured prompts to said display, responsive to said information at said keypad to provide said second preconfigured prompts, responsive to said information and said choices among said second preconfigured prompts to process said information and said plurality of preconfigured responses with said medical data in said memory to produce said medical answer, and operable to provide said medical answer to said display.

13. The handheld medical calculator and reference device as claimed in claim 12 wherein:

said display is capable of displaying a plurality of second preconfigured prompts and a plurality of information adjacent to and related to said plurality of second preconfigured prompts, said display is capable of displaying at least one first preconfigured prompt related to said predetermined medical question;

said keypad has at least one key capable of being operatively associated with said display and said at least one first preconfigured prompt; and said processor is operable to establish the operative association of said at least one key with said at least one first preconfigured prompt on said display.

14. The handheld medical calculator and reference device as claimed in claim 12 wherein:

said display is capable of displaying a plurality of second preconfigured prompts and a plurality of information adjacent to and related to said plurality of second preconfigured prompts, and said display is capable of simultaneously displaying all of said second preconfigured prompts and all of said input information related to said predetermined medical question.

15. The handheld medical calculator and reference device as claimed in claim 12 wherein:

said memory contains drug dosage information;

said processor includes a calculator;

said processor is responsive to said keypad inputting a drug question to provide preconfigured prompts for prescription, patient weight, renal insufficiency, and drug concentration information;

said processor is responsive to said keypad inputting said prescription, patient weight, renal insufficiency, and drug concentration information to use said information and said drug dosage information from said memory to calculate a drug dosage answer with adjustment for body surface area and weight; and said processor is operable to cause said display to output said drug dosage answer.

16. The handheld medical calculator and reference device as claimed in claim 12 wherein:

said memory contains drug infusion information;

said processor includes a calculator;

said processor is responsive to said keypad inputting a drug infusion question to provide preconfigured prompts for prescription, patient weight, renal insufficiency, and drug concentration information;

said processor is responsive to said keypad inputting said prescription, patient weight, renal insufficiency, and drug concentration information to use said information and said drug infusion information from said memory to calculate a drug infusion answer with adjustment for body surface area and weight; and said processor is operable to cause said display to output said drug infusion answer.

17. The handheld medical calculator and reference device as claimed in claim 12 wherein:

said memory contains respiratory and pulmonary nomograms and information;

said processor includes a calculator;

said processor is responsive to said keypad inputting a respiratory or pulmonary question to provide said second preconfigured prompts to ask ventilation parameters questions;

said processor is responsive to said keypad inputting said ventilation parameters question to provide further preconfigured prompts for relevant patient data;

said processor is responsive to say keypad inputting said relevant patient data to use said nomogram to determine body surface area and respiration rate;

said processor is responsive to say keypad inputting said relevant patient data to calculate minute ventilation and tidal volume; and said processor is operable to cause said display to output said minute ventilation, tidal volume, and respiration rate.

18. The handheld medical calculator and reference device as claimed in claim 12 wherein:

said memory contains respiratory and pulmonary mapping and information;

said processor includes a calculator;

said processor is responsive to said keypad inputting a respiratory or pulmonary question to provide said second preconfigured prompts to ask a vital capacity question;

said processor is responsive to said keypad inputting said vital capacity question to provide further preconfigured prompts for relevant patient data;

said processor is responsive to say keypad inputting said relevant patient data to calculate said vital capacity; and said processor is operable to cause said display to output said vital capacity and mapping.

19. The handheld medical calculator and reference device as claimed in claim 12 wherein:

said memory contains acid-base information and an acid-base nomogram;

said processor includes a calculator;

said processor is responsive to said keypad inputting an acid-base question to cause said display to output said second preconfigured prompts on acid-base equations, acid-base disorders, and other acid-base related quantities;

said processor is responsive to keypad input of said acid-base equations, acid-base disorders, and other acid-base related quantities and said acid-base information and said acid-base nomogram from said memory to determine acid-base solutions, list acid-base disorders, and calculated acid-base related quantities; and said processor is operable to cause said display to output acid-base solutions, list acid-base disorders, and calculated acid-base related quantities.

20. The handheld medical calculator and reference device as claimed in claim 12 wherein:

said memory contains medical information and a medical nomogram;

said processor includes a calculator;

said processor is responsive to said keypad inputting a medical question to use said medical information and said medical nomogram from said memory to provide a recommended treatment; and said processor is operable to cause said display to output said recommended treatment.

21. The handheld medical calculator and reference device as claimed in claim 12 wherein:

said memory contains cardiac information;

said processor includes a calculator;

said processor is responsive to said keypad inputting a cardiac question to provide said second preconfigured prompts for cardiac function tests, cardiac work indices, and vascular resistance;

said processor is responsive to said keypad inputting said cardiac function tests, cardiac work indices, and vascular resistance to provide further preconfigured prompts for patient information;

said processor is responsive to said patient information to calculate said cardiac function tests, cardiac work indices, and vascular resistance; and said processor is operable to cause said display to output said cardiac function tests, cardiac work indices, and vascular resistance.

22. The handheld medical calculator and reference device as claimed in claim 12 wherein:

said memory contains hemodynamic information;

said processor includes a calculator;

said processor is responsive to said keypad inputting a hemodynamic question to provide said second preconfigured prompts for patient information, pressure data, or heart data;

said processor is responsive to said keypad inputting said patient information, pressure data, or heart data to indicate missing information or data;

said processor is responsive to said missing information or data to calculate said missing information or data; and said processor is operable to cause said display to output completed patient information, pressure data, or heart data.

23. The handheld medical calculator and reference device as claimed in claim 12 wherein:

said memory contains nutritional information;

said processor includes a calculator;

said processor is responsive to said keypad inputting a nutritional question to provide said second preconfigured prompts for metabolic, assessment, and hyperalimentation determinations;

said processor is responsive to said keypad inputting said for metabolic, assessment, and hyperalimentation determinations to calculate basal metabolic rate, basal energy expenditure, nitrogen balance, BUN/urea conversion, lean body mass, ideal body weight, or time, concentrations, and flow rate for nutrients; and said processor is operable to cause said display to output said basal metabolic rate, basal energy expenditure, nitrogen balance, BUN/urea conversion, lean body mass, ideal body weight, or time, concentrations, and flow rate for nutrients.

24. The handheld medical calculator and reference device as claimed in claim 12 wherein:

said processor is responsive to the input of patient data to store such patient data in said memory; and said processor is responsive to said keypad inputting a patient question to retrieve said patient data from said memory and cause said display to output said patient data.

* * * * *